(12) United States Patent  
Einav

(10) Patent No.: US 8,888,723 B2  
(45) Date of Patent: Nov. 18, 2014

(54) GAIT REHABILITATION METHODS AND APPARATUSES

(75) Inventor: Omer Einav, Kfar Monash (IL)

(73) Assignee: Motorika Limited, Hamilton (BM)

( * ) Notice: Subject to any disclaimer, the term of this patent is extended or adjusted under 35 U.S.C. 154(b) by 1783 days.

(21) Appl. No.: 10/597,635

(22) PCT Filed: Feb. 4, 2005

(86) PCT No.: PCT/IL2005/000138  
§ 371 (c)(1),  
(2), (4) Date: May 8, 2008

(87) PCT Pub. No.: WO2005/074370  
PCT Pub. Date: Aug. 18, 2005

(65) Prior Publication Data  
US 2008/0234113 A1    Sep. 25, 2008

Related U.S. Application Data

(60) Provisional application No. 60/542,022, filed on Feb. 5, 2004, provisional application No. 60/633,428, filed on Dec. 7, 2004, provisional application No. 60/633,429, filed on Dec. 7, 2004, provisional application No. 60/633,442, filed on Dec. 7, 2004.

(51) Int. Cl.  
*A61H 1/00* (2006.01)  
*A61H 1/02* (2006.01)  
(Continued)

(52) U.S. Cl.  
CPC ....... *A61B 5/6887* (2013.01); *A61H 2201/5064* (2013.01); *A61H 1/0259* (2013.01);  
(Continued)

(58) Field of Classification Search  
CPC ......... A61H 1/00; A61H 1/02; A61H 1/0214; A61H 1/0255; A61H 1/0259; A61H 1/0266; A61H 3/008; A61H 2001/0203; A61H 2001/01115; A61H 2001/5061; A61H 2001/5064; A61H 2001/5071; A61H 2001/5079; A61H 2001/5084; A61H 2203/0406; A61H 2203/0425; A61H 2201/5092; A61H 1/0237; A61B 5/112  
USPC ............ 601/5, 23, 24, 26–32, 33–36; 482/66, 482/92, 142, 79; 128/898  
See application file for complete search history.

(56) References Cited

U.S. PATENT DOCUMENTS 3,745,990 A    7/1973    Neis  
3,824,991 A    7/1974    Whitaker  
(Continued)

FOREIGN PATENT DOCUMENTS

DE    10133572    4/2002  
EP    0304538    3/1989  
(Continued)

OTHER PUBLICATIONS

Official Action Dated May 9, 2011 From the US Patent and Trademark Office Re.: U.S. Appl. No. 11/568,463.

(Continued)

*Primary Examiner* — Quang D Thanh

(57) ABSTRACT

A method for gait rehabilitation, comprising, identifying at least one deficient gait element; exercising said deficient gait element individually using a rehabilitation apparatus; and exercising said deficient gait element in concert with at least one other gait element using said rehabilitation apparatus.

38 Claims, 9 Drawing Sheets

(51) Int. Cl.
  *A61B 5/11* (2006.01)
  *A61B 5/103* (2006.01)
  *A61H 3/00* (2006.01)
  *A61B 5/00* (2006.01)
  *A61B 5/0488* (2006.01)

(52) U.S. Cl.
  CPC ........ *A61H 2201/5071* (2013.01); *A61H 3/008* (2013.01); *A61B 5/1116* (2013.01); *A61B 5/6831* (2013.01); *A61H 2203/0406* (2013.01); *A61H 1/0255* (2013.01); *A61H 2001/0203* (2013.01); *A61H 2201/5061* (2013.01); *A61H 1/0266* (2013.01); *A61B 5/103* (2013.01); *A61H 2201/0115* (2013.01); *A61H 2201/5079* (2013.01); *A61B 5/04884* (2013.01); *A61H 2203/0425* (2013.01); *A61H 2201/5084* (2013.01); *A61B 2505/09* (2013.01); *A61B 5/702* (2013.01); *A61H 1/0237* (2013.01)
  USPC ........ 601/32; 601/5; 601/23; 601/27; 601/33; 601/35; 128/898; 482/79

(56) References Cited

U.S. PATENT DOCUMENTS

| | | | |
|---|---|---|---|
| 3,919,691 A | 11/1975 | Noll | |
| 3,929,462 A | 12/1975 | Karmin | |
| 4,099,697 A | 7/1978 | Von Schuckmann | |
| 4,499,900 A | 2/1985 | Petrofsky et al. | |
| 4,582,049 A | 4/1986 | Ylvisaker | |
| 4,685,928 A | 8/1987 | Yaeger | |
| 4,691,694 A | 9/1987 | Boyd et al. | |
| 4,724,842 A | 2/1988 | Charters et al. | |
| 4,765,610 A | 8/1988 | Sidwell | |
| 4,773,398 A | 9/1988 | Tatom | |
| 4,824,104 A | 4/1989 | Bloch | |
| 4,883,067 A | 11/1989 | Knispel et al. | |
| 4,921,244 A | 5/1990 | Berroth | |
| 4,936,299 A | 6/1990 | Erlandson | |
| 4,966,413 A | 10/1990 | Palarski | |
| 5,048,826 A | 9/1991 | Ryan | |
| 5,070,873 A | 12/1991 | Graupe et al. | |
| 5,158,074 A | 10/1992 | Grellas | |
| 5,179,939 A | 1/1993 | Donovan et al. | |
| 5,193,539 A | 3/1993 | Schulman et al. | |
| 5,193,540 A | 3/1993 | Schulman et al. | |
| 5,201,772 A | 4/1993 | Maxwell | |
| 5,211,161 A * | 5/1993 | Stef ................................. | 601/5 |
| 5,231,998 A | 8/1993 | Rosen et al. | |
| 5,244,441 A | 9/1993 | Dempster et al. | |
| 5,269,318 A | 12/1993 | Nashner | |
| 5,282,460 A | 2/1994 | Boldt | |
| 5,311,880 A | 5/1994 | Lancaster et al. | |
| 5,312,439 A | 5/1994 | Loeb | |
| 5,324,316 A | 6/1994 | Schulman et al. | |
| 5,343,856 A * | 9/1994 | Proctor ........................... | 601/35 |
| 5,358,251 A | 10/1994 | Ashton | |
| 5,391,128 A | 2/1995 | DeBear | |
| 5,397,865 A | 3/1995 | Park | |
| 5,405,367 A | 4/1995 | Schulman et al. | |
| 5,411,044 A | 5/1995 | Andolfi | |
| 5,413,611 A | 5/1995 | Haslam, II et al. | |
| 5,454,774 A | 10/1995 | Davis | |
| 5,466,213 A | 11/1995 | Hogan et al. | |
| 5,476,103 A | 12/1995 | Nahsner | |
| 5,476,428 A | 12/1995 | Potash et al. | |
| 5,616,104 A | 4/1997 | Mulenburg et al. | |
| 5,662,693 A | 9/1997 | Johnson et al. | |
| 5,690,389 A | 11/1997 | Ekman et al. | |
| 5,755,645 A | 5/1998 | Miller et al. | |
| 5,830,160 A | 11/1998 | Reinkensmeyer | |
| 5,836,304 A | 11/1998 | Kellinger et al. | |
| 5,846,086 A | 12/1998 | Bizzi et al. | |
| 5,853,353 A | 12/1998 | Blümel | |
| 5,919,115 A | 7/1999 | Horowitz et al. | |
| 5,954,621 A | 9/1999 | Joutras et al. | |
| 5,980,435 A | 11/1999 | Joutras et al. | |
| 6,004,244 A | 12/1999 | Simonson | |
| 6,035,465 A | 3/2000 | Rogozinski | |
| 6,051,017 A | 4/2000 | Loeb et al. | |
| 6,057,828 A | 5/2000 | Rosenberg et al. | |
| 6,061,004 A | 5/2000 | Rosenberg et al. | |
| 6,064,912 A | 5/2000 | Kenney | |
| 6,246,200 B1 | 6/2001 | Blumenkranz et al. | |
| 6,270,445 B1 | 8/2001 | Dean, Jr. et al. | |
| 6,379,393 B1 | 4/2002 | Mavroidis et al. | |
| 6,478,721 B1 | 11/2002 | Hunter | |
| 6,558,304 B1 | 5/2003 | Bardon et al. | |
| 6,592,315 B2 | 7/2003 | Osborne, Jr. | |
| 6,613,000 B1 | 9/2003 | Reinkensmeyer et al. | |
| 6,645,126 B1 | 11/2003 | Martin et al. | |
| 6,682,351 B1 | 1/2004 | Abraham-Fuchs et al. | |
| 6,774,885 B1 | 8/2004 | Even-Zohar | |
| 6,829,510 B2 | 12/2004 | Nathan et al. | |
| 6,839,594 B2 | 1/2005 | Cohen et al. | |
| 6,852,086 B2 | 2/2005 | Atlas et al. | |
| 6,870,438 B1 | 3/2005 | Shino et al. | |
| 6,966,882 B2 * | 11/2005 | Horst ................................. | 601/5 |
| 7,115,078 B1 | 10/2006 | Kalember et al. | |
| 7,163,488 B2 | 1/2007 | Anders et al. | |
| 7,209,788 B2 | 4/2007 | Nicolelis et al. | |
| 7,381,192 B2 | 6/2008 | Brodard et al. | |
| 7,504,577 B2 | 3/2009 | Riopelle | |
| 8,012,107 B2 | 9/2011 | Einav et al. | |
| 2002/0064438 A1 | 5/2002 | Osborne, Jr. | |
| 2002/0094913 A1 | 7/2002 | Valentino | |
| 2003/0032524 A1 | 2/2003 | Lamar et al. | |
| 2003/0199370 A1 | 10/2003 | Bucay-Bissu | |
| 2003/0208109 A1 | 11/2003 | David et al. | |
| 2003/0208246 A1 | 11/2003 | Kotlik et al. | |
| 2004/0102723 A1 | 5/2004 | Horst | |
| 2004/0106881 A1 * | 6/2004 | McBean et al. .................. | 601/5 |
| 2004/0172097 A1 | 9/2004 | Brodard et al. | |
| 2004/0180768 A1 | 9/2004 | Almada | |
| 2004/0245838 A1 | 12/2004 | Chiu | |
| 2005/0261114 A1 | 11/2005 | Heitzman et al. | |
| 2006/0149338 A1 | 7/2006 | Flaherty et al. | |
| 2006/0167564 A1 | 7/2006 | Flaherty et al. | |
| 2006/0229164 A1 | 10/2006 | Einav | |
| 2006/0277074 A1 | 12/2006 | Einav et al. | |
| 2006/0293617 A1 | 12/2006 | Einav et al. | |
| 2007/0282228 A1 | 12/2007 | Einav et al. | |
| 2007/0299371 A1 | 12/2007 | Einav et al. | |
| 2008/0132383 A1 | 6/2008 | Einav et al. | |
| 2008/0161733 A1 | 7/2008 | Einav et al. | |

FOREIGN PATENT DOCUMENTS

| | | |
|---|---|---|
| EP | 0569489 | 11/1993 |
| EP | 0703752 | 4/1996 |
| EP | 0862930 | 9/1998 |
| EP | 1145682 | 10/2001 |
| EP | 1364636 | 11/2003 |
| FR | 2809615 | 12/2001 |
| GB | 2357848 | 7/2011 |
| JP | 59-160455 | 9/1984 |
| JP | 60-200312 | 10/1985 |
| JP | 61-071984 | 4/1986 |
| JP | 61-217174 | 9/1986 |
| JP | 61-265151 | 11/1986 |
| JP | 01-316815 | 12/1989 |
| JP | 02-102652 | 4/1990 |
| JP | 05-007608 | 1/1993 |
| JP | 05-026209 | 4/1993 |
| JP | 06-505407 | 6/1994 |
| JP | 07-163626 | 6/1995 |
| JP | 08-322189 | 12/1996 |
| JP | 08-511448 | 12/1996 |
| JP | 03-039345 | 4/1997 |
| JP | 09-173499 | 7/1997 |
| JP | 3044600 | 10/1997 |
| JP | 3048540 | 2/1998 |
| JP | 10-207624 | 8/1998 |

(56) References Cited

FOREIGN PATENT DOCUMENTS

| | | |
|---|---|---|
| JP | 11-009574 | 1/1999 |
| JP | 11-155836 | 6/1999 |
| JP | 11-253504 | 9/1999 |
| JP | 2000-102523 | 4/2000 |
| JP | 2000-112335 | 4/2000 |
| JP | 2000-279463 | 10/2000 |
| JP | 3126901 | 11/2000 |
| JP | 2001-204850 | 7/2001 |
| JP | 3081786 | 8/2001 |
| JP | 2001-299842 | 10/2001 |
| JP | 2002-065891 | 3/2002 |
| JP | 2002-126019 | 5/2002 |
| JP | 2002-127058 | 5/2002 |
| JP | 3087629 | 5/2002 |
| JP | 2002-263213 | 9/2002 |
| JP | 2002-351993 | 12/2002 |
| JP | 2003-093451 | 4/2003 |
| JP | 2003-164544 | 6/2003 |
| JP | 2003-190235 | 7/2003 |
| JP | 2004-008751 | 1/2004 |
| JP | 2004-174692 | 6/2004 |
| WO | WO 92/13504 | 8/1992 |
| WO | WO 98/43700 | 8/1998 |
| WO | WO 98/37926 | 9/1998 |
| WO | WO 98/43701 | 10/1998 |
| WO | WO 98/46127 | 10/1998 |
| WO | WO 02/13673 | 2/2002 |
| WO | WO 02/35457 | 5/2002 |
| WO | WO 02/092164 | 11/2002 |
| WO | WO 03/023546 | 3/2003 |
| WO | WO 2004/050172 | 6/2004 |
| WO | WO 2005/074369 | 8/2005 |
| WO | WO 2005/074370 | 8/2005 |
| WO | WO 2005/074371 | 8/2005 |
| WO | WO 2005/074372 | 8/2005 |
| WO | WO 2005/074373 | 8/2005 |
| WO | WO 2005/075155 | 8/2005 |
| WO | WO 2005/086574 | 9/2005 |
| WO | WO 2005/087307 | 9/2005 |
| WO | WO 2005/105203 | 11/2005 |
| WO | WO 2006/021952 | 3/2006 |
| WO | WO 2006/061834 | 6/2006 |
| WO | WO 2006/082584 | 8/2006 |

OTHER PUBLICATIONS

Response Dated May 16, 2011 to Official Action of Mar. 15, 2011 From the US Patent and Trademark Office Re. U.S. Appl. No. 10/597,602.
Official Action Dated Jun. 15, 2010 From the US Patent and Trademark Office Re. U.S. Appl. No. 10/597,671.
Translation of Notification of Reasons for Rejection Dated Jun. 6, 2011 From the Japanese Patent Office Re. Application No. 2009-027772.
Official Action Dated Aug. 10, 2011 From the US Patent and Trademark Office Re. U.S. Appl. No. 10/597,633.
Official Action Dated Nov. 15, 2011 From the US Patent and Trademark Office Re. U.S. Appl. No. 10/597,633.
Response Dated Oct. 17, 2011 to Official Action of Jul. 18, 2011 From the US Patent and Trademark Office Re. U.S. Appl. No. 10/597,602.
Examination Report Dated Oct. 23, 2008 From the Instituto Mexicano de la Propriedad Industrial Re.: Application No. PA/a/2006/008919.
International Preliminary Report on Patentability Dated May 11, 2006 From the International Preliminary Examining Authority Re.: Application No. PCT/IL2005/000137.
International Preliminary Report on Patentability Dated Jan. 23, 2006 From the International Preliminary Examining Authority Re.: Application No. PCT/IL2005/000135.
International Search Report and the Written Opinion Dated Sep. 6 2006 From the International Searching Authority Re.: Application No. PCT/IL05/01318.
International Search Report and the Written Opinion Dated May 12, 2006 From the International Searching Authority Re.: Application No. PCT/IL05/00136.
International Search Report and the Written Opinion Dated Jul. 17, 2006 From the International Searching Authority Re.: Application No. PCT/IL05/00142.
International Search Report Dated Jun. 2, 2005 From the International Searching Authority Re.: Application No. PCT/IL2005/000139.
International Search Report Dated Feb. 3, 2006 From the International Searching Authority Re.: Application No. PCT/IL05/00140.
International Search Report Dated Jun. 8, 2006 From the International Searching Authority Re.: Application No. PCT/IL05/00906.
International Search Report Dated Nov. 17, 2005 From the International Searching Authority Re.: Application No. PCT/IL2005/000137.
International Search Report Dated Oct. 17, 2005 From the International Searching Authority Re.: Application No. PCT/IL05/00138.
International Search Report Dated Aug. 24, 2005 From the International Searching Authority Re.: Application No. PCT/IL2005/000442.
International Search Report Dated Nov. 28, 2005 From the International Searching Authority Re.: Application No. PCT/IL2005/00141.
International Searching Report Dated Jun. 3, 2005 From the International Searching Authority Re.: Application No. PCT/IL2005/000135.
Official Action Dated Feb. 7, 2008 From the US Patent and Trademark Office Re.: U.S. Appl. No. 11/389,773.
Official Action Dated May 19, 2008 From the US Patent and Trademark Office Re.: U.S. Appl. No. 11/207,655.
Official Action Dated Jul. 26, 2007 From the US Patent and Trademark Office Re.: U.S. Appl. No. 11/389,773.
Official Action Dated Sep. 30, 2008 From the US Patent and Trademark Office Re.: U.S. Appl. No. 11/207,655.
Supplementary Partial European Search Report Dated Jan. 29, 2008 From the European Patent Office Re.: Application No. 05774725.5.
Written Opinion Dated Jun. 2, 2005 From the International Searching Authority Re.: Application No. PCT/IL2005/000139.
Written Opinion Dated Feb. 3, 2006 From the International Searching Authority Re.: Application No. PCT/IL05/00140.
Written Opinion Dated Jun. 3, 2005 From the International Searching Authority Re.: Application No. PCT/IL2005/000135.
Written Opinion Dated Jun, 8, 2006 From the International Searching Authority Re.: Application No. PCT/IL05/00906.
Written Opinion Dated Nov. 17, 2005 From the International Searching Authority Re.: Application No. PCT/IL2005/000137.
Written Opinion Dated Oct. 17, 2005 From the International Searching Authority Re.: Application No. PCT/IL05/00138.
Written Opinion Dated Aug. 24, 2005 From the International Searching Authority Re.: Application No. PCT/IL2005/000442.
Written Opinion Dated Nov. 28, 2005 From the international Searching Authority Re.: Application No. PCT/IL05/00141.
Russo "An Other Reality", Maariv, p. 14, Oct. 26, 2004. Hebrew Onl!
Official action dated Sep. 14, 2010 from the US patent and trademark office re. U.S. Appl. No. 10/597,756.
Response dated Sep. 27, 2010 to notification of reasons for rejection of Jul. 12, 2010 from the Japanese patent office re. Application No. 2006-215045.
Response dated Sep. 22, 2010 to notification of reasons of rejection of May 26, 2010 from the Japanese patent office re. Application No. 2006-552013.
Response dated Sep. 26, 2010 to notification of reason for rejection of Jul. 9, 2010 from the Japanese patent office re. Application No. 2006-552014.
Response dated Sep. 27, 2010 to official action of Jun. 28, 2010 from the us patent and trademark office re.: U.S. Appl. No. 11/568,463.
Translation of notification of reason for rejection dated Aug. 13, 2010 from the Japanese patent office re. Application No. 2006-552009.
Response Dated Dec. 1, 2011 to Official Action of Sep. 1, 2011 From the US Patent and Trademark Office Re.: U.S. Appl. No. 11/883,663.
Official Action Dated Dec. 7, 2011 From the US Patent and Trademark Office Re.: U.S. Appl. No. 11/660,965.

(56) References Cited

OTHER PUBLICATIONS

Harwin et al. "Clinical Potential and Design of Programmable Mechanical Impedances for Orthotic Applications", Robotica, 16: 523-530, 1998.
Weiskopf et al. "Principles of a Brain-Computer Interface (BCI) Based on Real-Time Functional Magnetic Resonance Imaging (FMRI)", IEEE Transactions on Biomedical Engineering, 51(6): 966-970, Jun. 2004.
Yoo et al. "Drain-Computer Interface Using FMRI: Spatial Navigation by Thoughts", Clinical Neuroescience and Neuropathology, 15(10): 1591-1595, Jul. 19, 2004.
Amendment Dated Oct. 28, 2011 in Response to Decision of Rejection Dated Jun. 30, 2011 From the Japanese Patent Office Re: Application No. 2007-510233.
Notice of Allowance Dated Dec. 23, 2011 From the US Patent and Trademark Office Re.: U.S. Appl. No. 11/883,663.
Notice of Appeal Dated Oct. 28, 2011 in Response to Decision of Rejection Dated Jun. 30, 2011 From the Japanese Patent Office Re. Application No. 2007-510233.
Official Action Dated Jan. 11, 2012 From the US Patent and Trademark Office Re. U.S. Appl. No. 10/597,602.
Translation of Notification of Reasons for Rejection Dated Dec. 21, 2011 From the Japanese Patent Office Re. Application No. 2006-552015.
Translation of Official Query Dated Dec. 16, 2011 From the Japanese Patent Office Re. Application No. 2007-529131.
Abe et al. "ICA. A Study of EEG Analysis Method Using ICA", Proceedings of the 1999 IEICE General Conference, p. 149, 1999.
Translation of Notification of Reasons of Rejection Dated Jun. 12, 2009 From the Japanese Patent Office Re.: Application No. 2006-552011.
Translation of Notification of Reasons of Rejection Dated Sep. 14, 2009 From the Japanese Patent Office Re.: Application No. 2006-552014.
Translation of Questioning Dated Jan. 13, 2012 From the Japanese Patent Office Re. Application No. 2006-552013.
Translation of Questioning Dated May 25, 2011 From the Japanese Patent Office Re. Application No. 2006-552015.
Official Action Dated Jun. 28, 2010 From the US Patent and Trademark Office Re.: U.S. Appl. No. 11/568,463.
Translation of Notification of Reasons of Rejection Dated May 26, 2010 From the Japanese Patent Office Re. Application No. 2006-552013.
Translation of Notice of Reason for Rejection Dated Jun. 4, 2010 From the Japanese Patent Office Re. Application No. 2007-529131.
Official Action Dated Jul. 18, 2011 From the US Patent and Trademark Office Re. U.S. Appl. No. 10/597,602.
Response Dated Aug. 9, 2011 to Questioning of May 25, 2011 From the Japanese Patent Office Re. Application No. 2006-552015.
Examination Report Dated Aug. 25, 2011 From the Government of India, Patent Office Intellectual Property Building Re.: Application No. 3230/CHENP/2006.
Examination Report Dated Aug. 25, 2011 From the Government of India, Patent Office, Intellectual Property Building Re. Application No. 3232/CHENP/2006.
Examination Report Dated Aug. 25, 2011 From the Government of India, Patent Office, Intellectual Property Building Re.: Application No. 3231/CHENP/2006.
Response Dated Aug. 24, 2011 to Notification of Reasons for Rejection of Jun. 6, 2011 From the Japanese Patent Office Re. Application No. 2009-027772.
Official Action Dated Sep. 1, 2011 From the US Patent and Trademark Office Re.: U.S. Appl. No. 11/568,463.
Official Action Dated Sep. 23, 2011 From the US Patent and Trademark Office Re. U.S. Appl. No. 10/597,671.
Response Dated Sep. 26, 2011 to Notification of Reasons of Rejection of Jul. 4, 2011 From the Japanese Patent Office Re. Application No. 2006-552013.
Response Dated Oct. 5, 2011 to Notification of Reason for Rejection of Apr. 7, 2011 From the Japanese Patent Office Re. Application No. 2006-552014.
Notice of Allowance Dated Oct. 19, 2011 From the Japanese Patent Office Re. Application No. 2006-215045 and Its Translation Into English.
Response Dated Oct. 10, 2011 to Official Action of Aug. 10, 2011 From the US Patent and Trademark Office Re. U.S. Appl. No. 10/597,633.
Official Action Dated Oct. 7, 2011 From the US Patent and Trademark Office Re.: U.S. Appl. No. 11/568,463.
Official Action Dated Oct. 1, 2008 From the US Patent Office Re.: U.S. Appl. No. 11/389,773.
Official Action Dated Jul. 22, 2008 From the US Patent Offcie Re.: U.S. Appl. No. 11/389,773.
Supplemental Notice of Allowability Dated Aug. 9, 2011 From the US Patent and Trademark Office Re.: U.S. Appl. No. 10/597,675.
Official Action Dated Jan. 27, 2012 From the US Patent and Trademark Office Re. U.S. Appl. No. 10/597,605.
Translation of Notification of Reasons for Rejection Dated Dec. 15, 2010 From the Japanese Patent Office Re. Application No. 2009-027772.
Response Dated Jun. 14, 2011 to Notification of Reason for Rejection of Feb. 3, 2011 From the Japanese Patent Office Re. Application No. 2006-552009.
Translation of Decision of Rejection Dated Jun. 30, 2011 From the Japanese Patent Office Re. Application No. 2007-510233.
Official Action Dated Jul. 7, 2010 From the US Patent and Trademark Office Re.: U.S. Appl. No. 10/597,675.
Translation of Notification of Reason for Rejection Dated Jul. 9, 2010 From the Japanese Patent Office Re. Application No. 2006-552014.
Official Action Dated Jun. 15, 2011 From the US Patent and Trademark Office Re. U.S. Appl. No. 10/597,671.
Official Action Dated Dec. 29, 2008 From the US Patent and Trademark Office Re.: U.S. Appl. No. 11/792,477.
Response Dated Sep. 20, 2010 to Notice of Reason for Rejection of Jun. 4, 2010 From the Japanese Patent Office Re. Application No. 2007-529131.
Translation of Notification of Reasons of Rejection Dated Jul. 4, 2011 From the Japanese Patent Office Re. Application No. 2006-552013.
Response Dated Jul. 6, 2011 to the Notification of Reasons for Rejection of Apr. 6, 2011 From the Japanese Patent Office Re. Application No. 2006-215045.
Response Dated Jun. 9, 2011 to Official Action of May 9, 2011 From the US Patent and Trademark Office Re.: U.S. Appl. No. 11/568,463.
Response Dated Jul. 12, 2011 to Official Action of Jun. 15, 2011 From the US Patent and Trademark Office Re. U.S. Appl. No. 10/597,671.
Response Dated Jul. 18, 2011 to Official Action of Mar. 16, 2011 From the US Patent and Trademark Office Re.: U.S. Appl. No. 11/568,463.
Notice of Reasons for Rejection Dated Aug. 31, 2011 From the Japanese Patent Office Re. Application No. 2006-552009 and Its Translation Into English.
Official Action Dated Sep. 1, 2011 From the US Patent and Trademark Office Re.: U.S. Appl. No. 11/660,965.
Response Dated Nov. 9, 2011 to Notice of Reasons for Rejection of Aug. 31, 2011 From the Japanese Patent Office Re. Application No. 2006-552009.
Notice of Allowance Dated Feb. 16, 2011 From the US Patent and Trademark Office Re.: U.S. Appl. No. 10/597,675.
Translation of Notification of Reason for Rejection Dated Apr. 7, 2011 From the Japanese Patent Office Re. Application No. 2006-552014.
Translation of Notification of Reasons for Rejection Dated Apr. 6, 2011 From the Japanese Patent Office Re. Application No. 2006-215045.
Official Action Dated Mar. 15, 2011 From the US Patent and Trademark Office Re. U.S. Appl. No. 10/597,602.
Response Dated Feb. 22, 2011 to Official Decision of Rejection of Oct. 29, 2010 From the Japanese Patent Office Re. Application No. 2007-529131.

(56) References Cited

OTHER PUBLICATIONS

Amendment Dated Oct. 28, 2011 in Response to Decision of Rejection Dated Jun. 30, 2011 From the Japanese Patent Office Re. Application No. 2007-510233.
Response Dated Nov. 1, 2010 to Decision of Rejection of Jul. 9, 2010 From the Japanese Patent Office Re. Application No. 2006-552015.
Response Dated Dec. 6, 2010 to Official Action of Jul. 7, 2010 From the US Patent and Trademark Office Re.: U.S. Appl. No. 10/597,675.
Translation of Decision of Rejection Dated Jul. 9, 2010 From the Japanese Patent Office Re. Application No. 2006-552015.
Translation of Official Decision of Rejection Dated Oct. 29, 2010 From the Japanese Patent Office Re. Application No. 2007-529131.
Response Dated Oct. 3, 2011 to Official Action of Sep. 1, 2011 From the US Patent and Trademark Office Re.: U.S. Appl. No. 11/660,965.
Proceedings Further With the European Patent Applicaiton Pursuant to Rule 70(2) EPC Dated Feb. 23, 2012 From the European Patent Office Re. Application No. 05703181.7.
Supplementary European Search Report Dated Feb. 6, 2012 From the European Patent Office Re. Application No. 05703181.7.
Official Action Dated Mar. 16, 2011 From the US Patent and Trademark Office Re.: U.S. Appl. No. 11/568,463.
Proceeding Further With the European Patent Application Pursuant to Rule 70(2) EPC Dated Jul. 31, 2009 From the European Patent Office Re.: Application No. 06704564.1.
Translation of Notification of Reasons of Rejection Dated Mar. 9, 2010 From the Japanese Patent Office Re.: Application No. 2006-552008.
International Preliminary Report on Patentability Dated Apr. 21, 2010 From the International Preliminary Examining Authority Re.: Application No. PCT/IL05/00138.
Response Dated Aug. 4, 2010 to Notification of Reasons of Rejection of Mar. 9, 2010 From the Japanese Patent Office Re.: Application No. 2006-552008.
Translation of Notification of Reasons for Rejection Dated Jul. 12, 2010 From the Japanese Patent Office Re. Application No. 2006-215045.
Response Dated Apr. 6, 2011 to Notification of Reasons for Rejection of Jan. 27, 2011 From the Japanese Patent Office Re. Application No. 2007-510233.
Response Dated Apr. 10, 2011 to Notification of Reasons for Rejection of Dec. 15, 2010 From the Japanese Patent Office Re. Application No. 2009-027772.
Communication Pursuant to Article 96(2) Dated Dec. 11, 2006 From the European Patent Office Re.: Application No. 05703180.9.
Examination Report Dated Oct. 29, 2008 From the Instituto Mexicano de la Propriedad Industrial Re.: Application No. PA/a2006/008914.
International Preliminary Report on Patentability Dated Aug. 16, 2007 From the International Bureau of WIPO Re.: Application No. PCT/IL2006/000140.
International Preliminary Report on Patentability Dated Jan. 19, 2007 From the International Preliminary Examining Authority Re.: Application No. PCT/IL05/00138.
International Preliminary Report on Patentability Dated Apr. 26, 2007 From the International Bureau of WIPO Re.: Application No. PCT/IL2005/000139.
International Preliminary Report on Patentability Dated Sep. 29, 2008 From the International Preliminary Examining Authority Re.: Application No. PCT/IL06/00140.
International Search Report and the Written Opinion Dated Jan. 3, 2007 From the International Searching Authority Re.: Application No. PCT/IL06/00140.
Office Action Dated Sep. 26, 2008 From the State Intellectual Properety Office of the People's Republic of China Re.: Application No. 20580010391.4.
Official Action Dated Oct. 1, 2008 From the US Patent and Trademark Office Re.: U.S. Appl. No. 11/389,773.
Communication of Results From Examination Dated Oct. 23, 2008 From the Instituto Mexicano de la Propriedad Industrial Re.: Application No. PA/a/2006/008914 and its Translation into English.

Communication Pursuant to Article 94(3) EPC Dated Oct. 12, 2009 From the European Patent Office Re.: Application No. 06704564.1.
International Preliminary Report on Patentability Dated Mar. 8, 2007 From the International Bureau of WIPO Re.: Application No. PCT/IL2005/000906.
International Preliminary Report on Patentability Dated Jun. 12, 2006 From the International Preliminary Examining Authority Re.: Application No. PCT/IL2005/000442.
International Preliminary Report on Patentability Dated Aug. 17, 2006 From the International Bureau of WIPO Re.: Application No. PCT/IL2005/000136.
International Preliminary Report on Patentability Dated Aug. 17, 2006 From the International Bureau of WIPO Re.: Application No. PCT/IL2005/000140.
International Preliminary Report on Patentability Dated Aug. 17, 2006 From the International Bureau of WIPO Re.: Application No. PCT/IL2005/000141.
International Preliminary Report on Patentability Dated Jun. 21, 2007 From the International Bureau of WIPO Re.: Application No. PCT/IL2005/001318.
Notification of Reasons of Rejection Dated Jun. 4, 2009 From the Japanese Patent Office Re.: Application No. 2006-552011.
Notification of Reasons of Rejection Dated Sep. 14, 2009 From the Japanese Patent Office Re.: Application No. 2006-552015 and Its Translation Into English.
Official Action Dated Dec. 18, 2009 From the US Patent and Trademark Office Re.: U.S. Appl. No. 11/348,128.
Official Action Dated Mar. 19, 2010 From the US Patent and Trademark Office Re.: U.S. Appl. No. 10/597,675.
Official Action Dated May 19, 2009 From the US Patent and Trademark Office Re.: U.S. Appl. No. 11/792,477.
Official Action Dated Oct. 23, 2008 From the Instituto Mexicano de la Propriedad Industrial, Divisional Direction of Patents Re.: Application No. PA/a/2006/008919 and Its Translation Into English.
Official Action Dated Jun. 24, 2009 From the US Patent and Trademark Office Re.: U.S. Appl. No. 11/207,655.
Response Dated Feb. 7, 2010 to Notification of Reasons of Rejection Dated Sep. 14, 2009 From the Japanese Patent Office Re.: Application No. 2006-552015.
Response Dated Feb. 9, 2010 to Notification of Reasons of Rejection of Sep. 14, 2009 From the Japanese Patent Office Re.: Application No. 2006-552014.
Response Dated Apr. 13, 2010 to Communication Pursuant to Article 94(3) EPC of Oct. 12, 2009 From the European Patent Office Re.: Application No. 06704564.1.
Translation of Office Action Dated Jan. 21, 2009 From the Japanese Patent Office Re.: Application No. 2006-552008.
Response Dated Apr. 19, 2010 to Official Action of Mar. 19, 2010 From the US Patent and Trademark Office Re.: U.S. Appl. No. 10/597,675.
Supplementary Partial European Search Report and the European Search Opinion Dated Jul. 14, 2009 From the European Patent Office Re.: Application No. 06704564.1.
Translation of Decision of Rejection Dated Feb. 1, 2011 From the Japanese Patent Office Re. Application No. 2006-552013.
Translation of Notification of Reason for Rejection Dated Feb. 3, 2011 From the Japanese Patent Office Re. Application No. 2006-552009.
Translation of Notification of Reasons for Rejection Dated Jan. 27, 2011 From the Japanese Patent Office Re. Application No. 2007-510233.
Backlife "The Backlife Idea", Product Information, <http://www.backlife.com>, 27 P., 2003.
Bak "The Complex Motion of Standing Still. Hydraulics, Sensors, and Human Modeling Dsta-Unified by Proprietary Software", <http://www.designnews.com/article/CA73202>, 5 P., 2001.
Burgar et al. "Development of Robots for Rehabilitation Therapy: The Palo Alto VA/Stanford Experience", Journal of Rehabilitation Research and Development, 37(6): 663-673, 2000.
Cameron et al. "Micromodular Implants to Provide Electrical Stimulation of Paralyzed Muscles and Limbs", IEEE Transactions on Biomedical Engineering, 44(9): 781-790, 1997. Abstract.

(56) References Cited

OTHER PUBLICATIONS

Graupe "EMG Pattern Analysis for Patient-Responsive Control of FES in Paraplegics for Walker-Supported Walking", IEEE Transactions on Biomedical Engineering, 36(7): 711-719, 1989. p. 711, 1-h col., Paragraph 1-r-h col., Paragraph 1, Figs.3, 5, p. 716, 1-h col., Figs.
Messinger "ReAbility Games: Island Hunt Catch'em Patrol Muzment", Detailed Specifications Document, NOKs Technologies, Version 1.0, 16 P., 2004.
Micromedical "BalanceQuest: Computerized Dynamic Posturography", Micromedical Technologies, <http://www.micromedial.com>, 6 P., 2001.
Motek "Motek Medical Rehabilitation: Rehabilitation", <http://www.e-motek.com>, 1 P.
Peasgood et al. "EMG-Controlled Dosed Loop Electrical Stimulation Using a Digital Signal Processor", Electronics Letters, 36(22): 1832-1833, 2000. p. 1832, 1-h col., Paragraph 1, Fig.l, p. 1833, r-h col., Paragraph 1.
Pfurtscheller et al. "Brain Oscillations Control Hand Orthosis in a Tetraplegic", Neuroscience Letters, 292: 211-214, 2000.
Richardson et al. "Comparing Smooth Arm Movement With the Two-Thirds Power Law and the Related Segmented-Control Hypothesis", The Journal of Neuroscience, 22(18): 8201-8211, 2002.
Viviani et al. "Minimum-Jerk, Two-Thirds Power Law, and Isochrony: Converging Approaches to Movement Planning", Journal of Experimental Psychology: Human Perception and Performance, 17: 32-53, 1995. Abstract.
Viviani et al. "Trajectory Determines Movement Dynamics", The Journal of Neuroscience, 7: 431-437, 1982.
Translation of Notification of Names of Appeal Examiners and Appeal Clerk Dated Jun. 6, 2012 From the Japanese Patent Office Re. Application No. 2006-552013.
Advisory Action Before the Filing of an Appeal Brief Dated Jul. 26, 2012 From the US Patent and Trademark Office Re. U.S. Appl. No. 10/597,633.
Invitation Pursuant to Rule 62a(1) and Rule 63(1) EPC Dated Mar. 20, 2012 From the European Patent Office Re. Application No. 05703185.8.
Communication Pursuant to Article 94(3) EPC Dated Feb. 8, 2012 From the European Patent Office Re. Application No. 05703179.1. Shino et al.
Invitation Pursuant to Rule 62a(1) EPC and Rule 63(1) EPC Dated Mar. 20, 2012 From the European Patent Office Re. Application No. 05703184.1.
Invitation Pursuant to Rule 62a(1) EPC and Rule 63(1) EPC Dated Mar. 20, 2012 From the European Patent Office Re. Application No. 05703183.3.
Notice of Allowance Dated Apr. 4, 2012 From the US Patent and Trademark Office Re. U.S. Appl. No. 10/597,599.
Official Action Dated Jul. 18, 2013 From the US Patent and Trademark Office Re. U.S. Appl. No. 10/597,633.
Communication Pursuant to Article 94(3) EPC Dated Mar. 19, 2013 From the European Patent Office Re. Application No. 05703183.3.
Communication Pursuant to Article 94(3) EPC Dated Mar. 19, 2013 From the European Patent Office Re. Application No. 05703184.1.
Communication Pursuant to Article 94(3) EPC Dated Mar. 19, 2013 From the European Patent Office Re. Application No. 05703185.8.
Notice of Allowance Dated Jun. 10, 2013 From the US Patent and Trademark Office Re. U.S. Appl. No. 10/597,671.
Advisory Action Before the Filing of An Appeal Brief Dated 26 Jul. 2012 From the US Patent and Trademark Office Re. U.S. Appl. No. 10/597,633.
Applicant-Initiated Interview Summary Dated Jun. 11, 2012 From the US Patent and Trademark Office Re. U.S. Appl. No. 10/597,633.
Applicant-Initiated Interview Summary Dated Jan. 23, 2013 From the US Patent and Trademark Office Re. U.S. Appl. No. 10/597,671.
Applicant-Initiated Interview Summary Dated Oct. 25, 2012 From the US Patent and Trademark Office Re. U.S. Appl. No. 10/597,602.
Communication Pursuant to Article 94(3) EPC Dated Jul. 3, 2012 From the European Patent Office Re. Application No. 05703181.7.

Communication Under Rule 71(3) EPC Dated Nov. 7, 2012 From the European Patent Office Re. Application No. 05703179.1.
Official Action Dated Aug. 1, 2012 From the US Patent and Trademark Office Re.: U.S. Appl. No. 10/597,605.
Official Action Dated Sep. 1, 2011 From the US Patent and Trademark Office Re.: U.S. Appl. No. 11/883,663.
Official Action Dated Sep. 7, 2012 From the US Patent and Trademark Office Re. U.S. Appl. No. 10/597,671.
Official Action Dated May 9, 2011 From the US Patent and Trademark Office Re.: U.S. Appl. No. 11/883,663.
Official Action Dated Jun. 14, 2012 From the US Patent and Trademark Office Re.: U.S. Appl. No. 11/660,965.
Official Action Dated May 14, 2012 From the US Patent and Trademark Office Re. U.S. Appl. No. 10/597,633.
Official Action Dated Jun. 15, 2012 From the US Patent and Trademark Office Re. U.S. Appl. No. 10/597,602.
Official Action Dated Nov. 27, 2012 From the US Patent and Trademark Office Re. U.S. Appl. No. 10/597,633.
Proceeding Further With the European Patent Application Pursuant to Rule 70(2) EPC Dated Jul. 30, 2012 From the European Patent Office Re. Application No. 05703185.8.
Proceedings Further With the European Patent Application Pursuant to Rule 70(2) EPC Dated Jul. 30, 2012 From the European Patent Office Re. Application No. 05703183.3.
Proceedings Further With the European Patent Application Pursuant to Rule 70(2) EPC Dated Jul. 30, 2012 From the European Patent Office Re. Application No. 05703184.1.
Response Dated Jun. 9, 2011 to Official Action of May 9, 2011 From the US Patent and Trademark Office Re.: U.S. Appl. No. 11/883,663.
Supplementary Partial European Search Report Dated Jul. 11, 2012 From the European Patent Office Re. Application No. 05703183.3.
Supplementary Partial European Search Report Dated Jul. 11, 2012 From the European Patent Office Re. Application No. 05703184.1.
Supplementary Partiel European Search Report Dated Jul. 11, 2012 From the European Patent Office Re. Application No. 05703185.8.
Translation of Notification of Names of Appeal Examiners and Appeal Clerk Dated Jul. 6, 2012 From the Japanese Patent Office Re. Application No. 2006-552013.
Yoo et al. "Brain-Computer Interface Using FMRI: Spatial Navigation by Thoughts", Clinical Neuroescience and Neuropathology, 15(10); 1591-1595, Jul. 19, 2004.
Applicant—initiated Interview Summary Dated Oct. 25, 2012 From the US Patent and Trademark Office Re. U.S. Appl. No. 10/597,602.
Official Action Dated Apr. 10, 2014 From the US Patent and Trademark Office Re. U.S. Appl. No. 10/597,605.
Communication Pursuant to Article 94(3) EPC Dated May 13, 2014 From the European Patent Office Re. Application No. 06704564.1.
Official Action Dated Mar. 19, 2014 From the US Patent and Trademark Office Re. U.S. Appl. No. 11/660,965.
Applicant-Initiated Interview Summary Dated Dec. 20, 2013 From the US Patent and Trademark Office Re. U.S. Appl. No. 10/597,633.
Notice of Allowance Dated Jan. 30, 2014 From the US Patent and Trademark Office Re. U.S. Appl. No. 10/597,633.
Applicant-Initiated Interview Summary Dated Aug. 1, 2014 From the US Patent and Trademark Office Re. U.S. Appl. No. 10/597,605.
Communication Pursuant to Article 94(3) EPC Dated Jul. 17, 2014 From the European Patent Office Re. Application No. 05703181.7.
Communication Pursuant to Article 94(3) EPC Dated Jul. 28, 2014 From the European Patent Office Re. Application No. 05703183.3.
Communication Pursuant to Article 94(3) EPC Dated Jul. 28, 2014 From the European Patent Office Re. Application No. 05703184.1.
Communication Pursuant to Article 94(3) EPC Dated Jul. 28, 2014 From the European Patent Office Re. Application No. 05703185.8.
Notice of Allowance Dated Sep. 9, 2014 From the US Patent and Trademark Office Re. U.S. Appl. No. 11/660,965.
Notice of Allowance Dated Aug. 25, 2014 From the US Patent and Trademark Office Re. U.S. Appl. No. 10/597,605.
Official Action Dated Aug. 4, 2014 From the US Patent and Trademark Office Re. U.S. Appl. No. 10/597,602.

(56) References Cited

OTHER PUBLICATIONS

Kristy et al. "A Robotic Arm 'Smart Exercise System': A Rehabilitation Therapy Modality", Engineering in Medicine and Biology Society, Proceedings of the Annual International Conference of the IEEE Engineering in Images of the Twenty-First Century, XP010088537, p. 1504-1505, 1989.

Martens et al. "A FRIEND for Assisting Handicapped People. The Semiautonomous Robotic System 'FRIEND' Consists of An Electric Wheelchair With A Robotic Arm and Utilizes A Speech Interface", IEEE Robotics & Automation Magazine, XP055130671, 8(1): 57-65, Mar. 1, 2001.

* cited by examiner

GAIT REHABILITATION METHODS AND APPARATUSES

RELATED APPLICATIONS

The present application is a US National Phase of PCT Application No. PCT/IL2005/000138, filed on Feb. 4, 2005.

This application also claims the benefit under 119(e) of U.S. Provisional Application No. 60/542,022 filed on Feb. 5, 2004, U.S. Provisional Application No. 60/633,428 filed on Dec. 7, 2004, U.S. Provisional Application No. 60/633,429 filed on Dec. 7, 2004, and U.S. Provisional Application No. 60/633,442 filed on Dec. 7, 2004, the disclosure of which are incorporated herein by reference. This application is also related to U.S. Provisional Applications 60/566,078 filed on Apr. 29, 2004; 60/566,079 filed on Apr. 29, 2004; and 60/604,615 filed on Aug. 25, 2004.

This application is also related to PCT applications PCT/IL2005/000137 entitled "Rehabilitation with Music"; PCT/IL2005/000135 entitled "Neuromuscular Stimulation"; PCT/IL2005/000139 entitled "Fine Motor Control Rehabilitation"; PCT/IL2005/000140 entitled "Methods and Apparatuses for Rehabilitation Exercise and Training"; PCT/IL2005/000141 entitled "Methods and Apparatus for Rehabilitation and Training"; and PCT/IL2005/000142 entitled "Methods and Apparatus for Rehabilitation and Training", all filed on Feb. 4, 2005. The disclosures of all these applications are incorporated herein by reference.

FIELD OF THE INVENTION

The present invention relates to methods and apparatuses for rehabilitation.

BACKGROUND OF THE INVENTION

Strokes, accidents and other medical conditions can cause a person to lose the ability to control gait, for example, how to walk or run. During a lengthy rehabilitation process, a patient is taught anew how to control the body parts that contribute to patient gait and locomotion.

One system for providing rehabilitation is described in U.S. Pat. No. 6,666,831 ("the '831 patent"). The '831 patent describes a robotic exoskeleton and a control system for driving the robotic exoskeleton, including a method for making and using the robotic exoskeleton and its control system. The robotic exoskeleton has sensors embedded in it which provide feedback to the control system. Feedback is used from the motion of the legs themselves, as they deviate from a normal gait, to provide corrective pressure and guidance. The position versus time is sensed and compared to a normal gait profile. Various normal profiles are obtained based on studies of the population for age, weight, height and other variables.

Another system for providing rehabilitation is described in U.S. Pat. No. 6,689,075 ("the '075 patent"). The '075 patent describes a support structure which supports powered lifting means for lifting a patient from a wheelchair and moving the patient over a powered treadmill where the patient is lowered onto the treadmill. A control panel with a mirror thereon is supported at one end of the support structure, and a touch screen data entry/display device is supported by the panel. Two similar housings are disposed at opposite sides of the treadmill. Each housing pivotally supports a support arm which can swing away from the treadmill to facilitate access to the treadmill. Each support arm pivotally supports a first depending arm, and a second depending arm is pivotally supported therefrom. A pair of servo motors are supported by each support arm and are drivingly connected to the first and second depending arms to independently move the depending arms about the pivot axes thereof. A first attachment cuff is connected to the first depending arm for attachment to a patient's leg just above the knee. A second attachment cuff is connected to the second depending arm for attachment to a patient's ankle. The support arms are vertically adjustable, and the attachment cuffs are horizontally adjustable. The first attachment cuff is vertically adjustable, and the second attachment cuff floats vertically relative to its depending arm. Control means is connected to the drive means for the treadmill and the servo motors which move the depending arms to cause the treadmill and the depending arms to operate in a coordinated manner to cause the legs of the patient to move in a desired gait. Sensor means is also provided for sensing the home position as well as possible over-travel of the knee joint of the device.

SUMMARY OF THE INVENTION

An aspect of some embodiments of the invention relates to rehabilitating patients by using the foot as a primary contact point. Focus on the foot can assist with balance training. In some embodiments, foot focused exercise enables rehabilitation activity to be conducted while in a seated position. Either foot, or both feet, can be optionally utilized as contact points between the patient and the rehabilitation system. In some embodiments of the invention, rotating at least one foot by the ankle in the x, y and z axes as part of the rehabilitation. In some embodiments of the invention, the use of the foot as a focal point allows the device to be smaller.

An aspect of some embodiments of the invention relates to selective and staged rehabilitation of a patient in order to improve the gait of a patient. Various operative components of a patient's gait can be specifically targeted and exercised to achieve patient gait improvement.

In an exemplary embodiment of the invention, there is provided a method for gait rehabilitation wherein a complex gait element is chosen from the group consisting of balance, overcoming obstacles, climbing steps, movement up slopes and varying speed.

In an exemplary embodiment of the invention, a selected side of the patient is selected for rehabilitation.

An aspect of some embodiments of the invention relates to providing the ability to receive rehabilitation to a patient while the patient is in a sitting position, especially for gait rehabilitation. The invention optionally includes systems which provide wheelchair access. Alternatively, an active chair is provided which moves up and down, rotates in various directions and optionally includes a separate back support. Also provided are special exercises designed for a patient in a sitting position. Optionally, rehabilitation is facilitated by standing exercises.

An aspect of some embodiments of the invention relates to facilitating patient entry and exit from an array of rehabilitation systems. In some cases, entry and exit can be eased by providing various pieces of a rehabilitation system with the ability to swing open to accept a large sized patient or a wheelchair, for example. In other exemplary embodiments, the chair back spoons the patient, which allows a sliding off and on of the patient with or without the armpit support, and/or pushes the patient forward into a special chair for rehabilitation therapy. In further exemplary embodiments, a belt is used to move the patient into position. Optionally, adjustable bars with armpit supports can lift a patient into rehabilitation position, or alternatively a chair which tips the patient into an exercise position is provided. Optionally, the patient is assisted into a standing position by the rehabilitation system.

An aspect of some embodiments of the invention relates to providing a harness for controllable weight support and additionally for hip rehabilitation. Optionally, the harness is used in combination with at least a seat. Optionally, the harness is used in combination with at least an armpit support.

An aspect of some embodiments of the invention relates to providing rehabilitation systems which are used in combination with a wheelchair, crutches, ski poles, a hiking stick, cane or walker in order to rehabilitate gait.

In an exemplary embodiment of the invention, there is provided rehabilitation therapy that retrains a patient in an extensive range of motion and/or on multiple axes.

In an exemplary embodiment of the invention, feedback is provided to the patient during exercise in order to facilitate rehabilitation. Optionally, feedback is adapted to the cognitive state of the patient.

An aspect of some embodiments of the invention relates to providing rehabilitation systems which are transportable and/or are small in size for use in locations including small clinics, nursing homes, residential homes or places of work, especially for gait rehabilitation. In an exemplary embodiment of the invention, a rehabilitation system is provided which is transportable by suitcase. Optionally, a rehabilitation system is provided which is usable from either side.

An aspect of some embodiments of the invention relates to a mechanism for foot exercising. In an exemplary embodiment of the invention, a foot pedal can move in both X and Z axes. Optionally, a motor is provided for linear motion in each axis, for example using a belt. In an exemplary embodiment of the invention, the mechanism can detect when weight of a patient is not placed on the pedal and reduce the applied force accordingly. In an exemplary embodiment of the invention, when the pedal moves along the X axis, simulating a contact with the floor, the pedal is supported by a track, thereby reducing motor power needs. Conversely, when the pedal is above the "floor" level, weight of the patient is typically lower, so smaller motors may be used. Possibly, with some patients more power will be required but optionally lower accuracy is used for patients which place their weight on a foot that is not on "floor" level.

There is thus provided in accordance with an exemplary embodiment of the invention, a method for gait rehabilitation, comprising:

identifying at least one deficient gait element;

exercising said deficient gait element individually using a rehabilitation apparatus; and exercising said deficient gait element in concert with at least one other gait element using said rehabilitation apparatus. Optionally, gait elements are chosen from a group consisting of feet, legs, hips, torso, shoulders, head, hands and arms.

In an exemplary embodiment of the invention, the method comprises exercising a complex gait. Optionally, a complex gait is chosen from the group consisting of balance, overcoming obstacles, moving backwards, movement on steps, turning, movement on slopes and varying speed.

In an exemplary embodiment of the invention, said gait rehabilitation is performed sitting down. Optionally, said gait rehabilitation is performed in a wheelchair.

In an exemplary embodiment of the invention, said gait rehabilitation is performed utilizing an object designed to assist with movement. Optionally, said object is selected from a group consisting of a walker, crutches, ski poles, a walking stick or a cane.

There is also provided in accordance with an exemplary embodiment of the invention, a method for gait rehabilitation, comprising:

detecting the positions of at least one gait element during movement;

recording the detected positions of the at least one gait element, wherein position recordings are made;

displaying said position recordings of the at least one gait element; and exercising at least one gait element based on said display of said recording. Optionally, a gait element is chosen from a group consisting of feet, legs, hips, torso, shoulders, head, hands and arms. Optionally, at least one position sensor is used for said detecting. Alternatively or additionally, at least one optical sensing device is used for said detecting. Alternatively or additionally, at least one position sensor and at least one optical sensing device is used for said detecting. Alternatively or additionally, said position recordings are of movements performed by a person undergoing rehabilitation. Alternatively or additionally, said position recordings are of movements performed by a person not undergoing rehabilitation.

In an exemplary embodiment of the invention, said exercising is analyzed in comparison to said position recordings. Optionally, additional exercise is performed based on said analysis.

There is also provide din accordance with an exemplary embodiment of the invention, apparatus for rehabilitation comprising:

a motorized pedal adapted to be moved in a plane perpendicular to a surface; and a track adapted to support said pedal and a weight of a patient of at least 40 Kg when said pedal moves at a line near and parallel to said surface.

There is also provided in accordance with an exemplary embodiment of the invention, apparatus for rehabilitation, comprising:

a first motor, wherein said first motor provides movement to components of the apparatus on an x-axis generally parallel to a surface;

a second motor, wherein said second motor provides movements to components of the apparatus on a z-axis generally perpendicular to a surface;

at least one foot pedal component, wherein said foot pedal is operationally connected to said first and second motors and wherein said foot pedal rotates in a plurality of axes. Optionally, the apparatus comprises a track for supporting a weight of a patient when said pedal travels along said x-axis with said z-axis being at a minimum value. Alternatively or additionally, the apparatus comprises a foot rest and when a weight of a patient is placed on said foot rest, said first and second motors vary the amount of movement force provided to said foot pedal component.

In an exemplary embodiment of the invention, said apparatus is adapted to be used in water.

In an exemplary embodiment of the invention, said apparatus is portable.

In an exemplary embodiment of the invention, said foot pedal is equipped with pressure sensors in order to gauge and analyze the patient's force applied on at least one location by a foot of the patient.

In an exemplary embodiment of the invention, said foot pedal has the capability to extend and retract along a y-axis perpendicular to said axes.

In an exemplary embodiment of the invention, turning is exercised by utilizing at least the rotational and extension capabilities of said foot pedal while the patient follows a hypothetical curved path.

In an exemplary embodiment of the invention, said foot rest is a treadmill.

In an exemplary embodiment of the invention, said foot rest is a second motorized foot pedal. Optionally, said apparatus varies the power to each of said pedals according to a placement of weight of said patient.

In an exemplary embodiment of the invention, said apparatus further comprises extending support legs for apparatus stability enhancement.

In an exemplary embodiment of the invention, said foot pedal can be attached to the apparatus at either side.

In an exemplary embodiment of the invention, the travel of said foot pedal in the z axis is 20-50 centimeters.

In an exemplary embodiment of the invention, said foot pedal is connected to the apparatus at the bottom of said foot pedal.

In an exemplary embodiment of the invention, said foot pedal is adapted to receive a prosthetic foot.

In an exemplary embodiment of the invention, said second foot pedal is adapted to receive a prosthetic foot.

In an exemplary embodiment of the invention, said motors vary movement to at least some components of said apparatus based on patient use of a walking aid. Optionally, said walking aid is selected from a group consisting of a cane, crutches, ski poles, a walking stick or a walker.

In an exemplary embodiment of the invention, said patient exercises with said apparatus while in a seated position.

There is also provided in accordance with an exemplary embodiment of the invention, apparatus for gait training, comprising:

at least one element adapted to move a foot of a patient;

at least one armpit support; and at least one motor adapted to move said armpit support such that a patient supported by said support is moved from a sitting posture to a standing posture.

There is also provided in accordance with an exemplary embodiment of the invention, apparatus for gait training, comprising:

at least one element adapted to move a foot of a patient;

at least one chair having a seating surface; and at least one motor adapted to tilt said seating surface. Optionally, said seat lifts while tilting. Alternatively or additionally, said chair rotates around a vertical axis. Alternatively or additionally, said apparatus comprises a backrest and wherein when said chair is moved by said motor, the relationship between said seat and said backrest varies. Optionally, said chair is provided with at least one torso support. Alternatively or additionally, said backrest is articulated.

There is also provided in accordance with an exemplary embodiment of the invention, a method of gait rehabilitation, comprising:

attaching a pedal to a foot of a patient; and automatically controlling the rotating said pedal to rehabilitate said patient. Optionally, said rotating is in at least two axes. Alternatively or additionally, the method comprises automatically controlling the translation said foot during said rotating.

In an exemplary embodiment of the invention, controlling the rotating comprises restricting the rotation range. Alternatively or additionally, controlling the rotating comprises restricting the rotation angle. Alternatively or additionally, controlling the rotating comprises applying a resistive force to rotation. Alternatively or additionally, controlling the rotating comprises causing said rotation. Alternatively or additionally, controlling the rotating comprises initiating said rotation and allowing the rotation to continue to completion of a desired amount.

In an exemplary embodiment of the invention, the method comprises rehabilitating two feet concurrently.

In an exemplary embodiment of the invention, said pedal is movable in a plane perpendicular to a surface and wherein said automatically controlling the rotation is responsive to movement of said pedal in said plane.

BRIEF DESCRIPTION OF THE FIGURES

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements or parts which appear in more than one figure are preferably labeled with a same or similar number in all the figures in which they appear, in which.

DETAILED DESCRIPTION OF EXEMPLARY EMBODIMENTS

Figure 1:
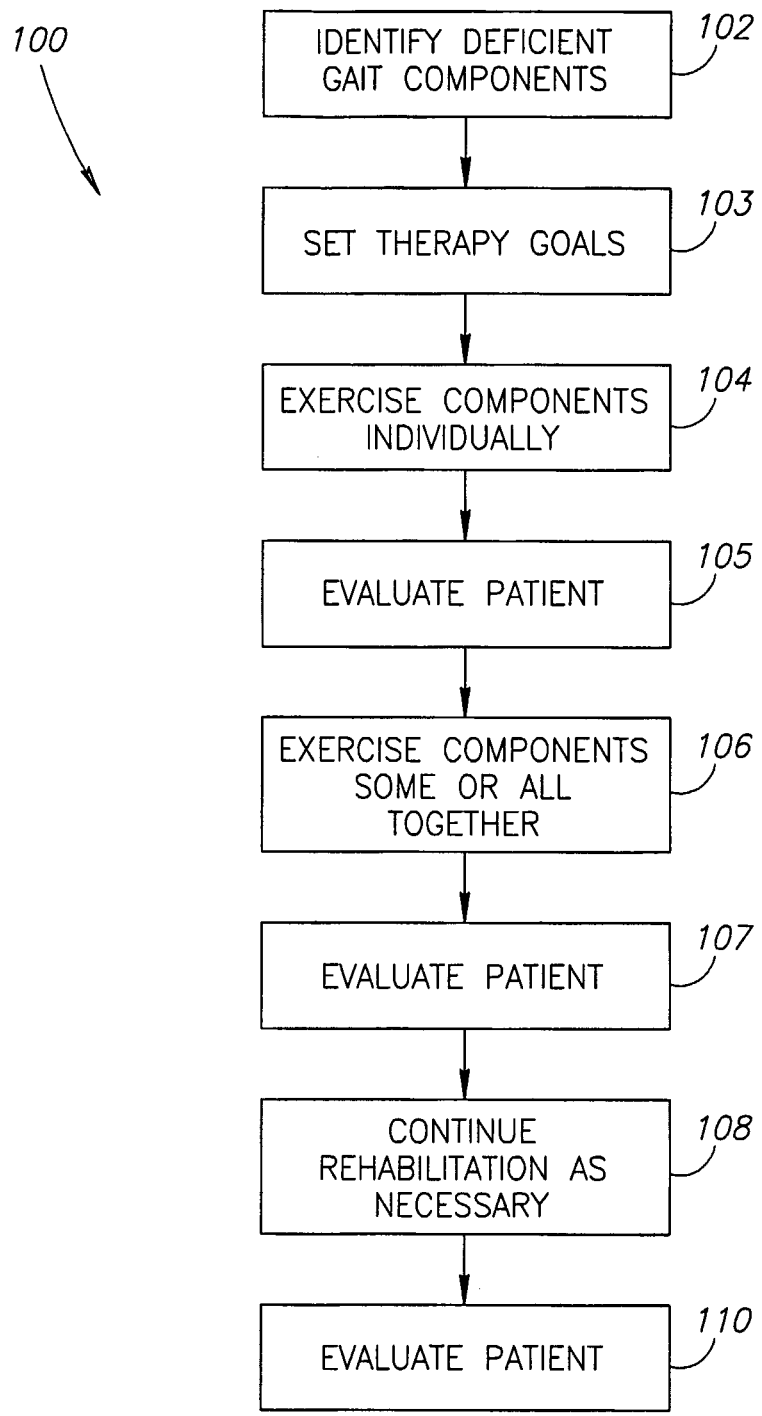
FIG. 1 is a flowchart depicting a method of gait rehabilitation of a patient in accordance with an exemplary embodiment of the invention.

Referring now to FIG. 1, a flowchart 100 is presented which sets forth a method of gait rehabilitation in an exemplary embodiment of the invention. At action 102, gait rehabilitation commences with the identification of deficient elements in a particular patient's gait. Optionally, the patient is exposed to various optional tests and/or exercises which help a rehabilitation assistant evaluate the extent of rehabilitation necessary to restore the patient's gait. Tests are optionally conducted in conjunction with the methods and apparatuses described herein and/or with methods and apparatuses known to those skilled in the art. In some exemplary embodiments of the invention, elements of a gait include foot and ankle movement, leg movement, hip movement, shoulder movement, arm movement, and more advanced elements such as balance, overcoming obstacles and varying speeds. Optionally, one or more of these elements are rehabilitated using the methods and apparatuses described herein. After the patient's baseline gait has been evaluated, therapy goals are set at action 103. It should be noted that goals can be set either before or after the initial evaluation at action 102. In addition, therapy goals can be changed throughout the therapy process as the patient rehabilitates depending on, for example, one or more of the patient's progress, options for rehabilitation and/or advances in rehabilitation medicine. Once deficient elements have been identified, at action 104 these deficient elements are optionally exercised individually possibly with the objective of increased control and/or strength. Optionally, the elements are trained in series. That is, each element is trained one after another. Optionally, some or all of the elements are trained in parallel. To wit, a plurality of elements are trained at the same time. At action 105, the patient's progress in rehabilitation is optionally reevaluated allowing for adjustments to be made in the rehabilitation process. Optionally, a patient's rehabilitation exercise is observed and/or supervised from a remote location by relaying data through a communications network, such as the Internet.

As the patient begins to master individual elements of a gait, some or all of these elements are optionally exercised together at action 106. In other words, the patient's abilities are optionally built up using individual elements at first, then adding elements in combination. The patient's progress in rehabilitation is optionally reevaluated allowing for adjustments to be made in the rehabilitation process at action 107. Complex gait attributes, such as overcoming obstacles and varying speeds, are optionally exercised at action 108. At action 110, the patient's progress in rehabilitation reevaluated allowing for adjustments to be made in the rehabilitation therapy process. Balance, as an element of gait, is optionally exercised at any or all of the actions 104-108. Optionally, any or all of the actions 104-108 are performed with a weight relieving apparatus or in water. Optionally, actions 105, 107 and 110 can be performed at any time during the rehabilitation process and can be combined or expanded to include more or less than three reevaluations. Optionally, exercise can be paused and resumed for any reason, including allowing the patient time to rest. The patient and/or a supervising health care professional can be provided with a switch which puts an apparatus into an operational/non-operational status. Optionally, a rehabilitation apparatus can be stopped at any time using a switch like a "dead-man switch".

Figure 2:
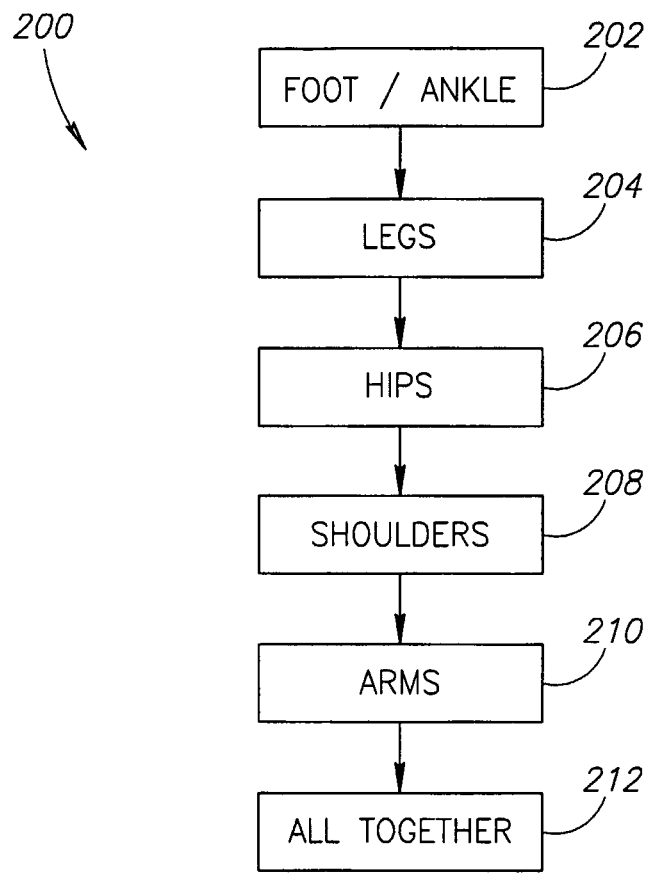
FIG. 2 is a flowchart depicting a progression of rehabilitative steps in accordance with an exemplary embodiment of the invention.

FIG. 2 depicts a flowchart 200 which illustrates a method of gait rehabilitation in an exemplary embodiment of the invention. For the purposes of this embodiment, a determination at action 102 has identified multiple deficiencies (e.g. foot/ankle, legs, hips, shoulders, arms, balance) in a particular patient's gait. A program of gait rehabilitation in this exemplary embodiment focuses on the gradual development of a patient's abilities. Therefore, the method commences at action 202 with foot and ankle exercises. In an exemplary embodiment of the invention, these foot and ankle exercises represent a basic building block in a patient's gait rehabilitation. Logically, the feet and ankles first need to be trained in order to allow the patient to stand up and bear weight on them. Optionally, foot and ankle exercises can be performed from the seated position, for example from a wheelchair. In some embodiments of the invention, exercises include moving the foot to pre-selected angles and rotations which help the patient achieve a particular gait (e.g. walking, climbing stairs, walking up a slope), exercises can also include asking the patient to exert a specific force on the foot pedal and/or asking the patient to shift weight from toe to ankle or from side to side, for example.

In an exemplary embodiment of the invention, an apparatus is provided that can accomplish at least these exercises. Optionally, these exercises are performed on a plurality of apparatuses. In an exemplary embodiment of the invention, an apparatus comprises robotic moving parts (e.g. robotic arms). Optionally, an exercise apparatus is provided with a controller. Optionally or additionally, the controller is a personal computer or a dedicated embedded computer. In an exemplary embodiment of the invention, the apparatus is provided with sensors which monitor at least the status of the patient and the apparatus. Optionally, the controller is connected to a communications network, such as the Internet, to allow for transmission of exercise related data to a remote location.

As foot control and strength develop, gait rehabilitation progresses with leg exercises at action 204. In an exemplary embodiment of the invention, the patient progresses from foot and ankle exercises to leg exercises in order to stand up. Leg exercises are optionally commenced from a sitting position and graduate to a standing position. Alternatively, leg exercises occur from a standing position. In other embodiments of the invention, leg exercises are performed while the patient is in a weight relieving apparatus, such as a harness. Depending on the patient's needs or the equipment available for rehabilitation, leg exercises can be performed on either leg, both legs simultaneously, only on one leg, or on only one leg at a time. In some exemplary embodiments of the invention, sensors are located on a rehabilitation apparatus which detect leg movement and analyze the leg movement achieved during exercise relative to recommended leg positions, or movement points. Additionally or alternatively, the drive system can measure and record the position and force/power of the motion as generated by the patient. Optionally, a patient's leg is attached to a rehabilitational apparatus at the foot, instead of a location on the leg, in order to practice leg exercises. Such an attachment can potentially provide a number of advantages, including assisting with balance training. For example, being attached for support at the leg provides the patient with unnatural and possibly rehabilitation hampering support. However, support from the foot is natural and usual as this support is usually derived from the floor on which the patient is standing.

In an exemplary embodiment of the invention, leg exercises can be performed in three basic modes of operation. The first mode is where motive force during rehabilitation is derived from the patient. This mode is likely used when the patient is nearing the end of rehabilitation or in the case where a healthy side or element is being observed in order to determine the rehabilitation goal for an unhealthy part of the patient. The second optional mode of operation is passive. That is, where the rehabilitation apparatus provides the motive force to the patient. This mode is likely used when the patient is at the beginning of rehabilitation and is still too weak, uncoordinated or the like to move the rehabilitation apparatus and/or the paretic body parts. In an exemplary embodiment, exercise is performed in this mode while the patient is in a harness. Exercise in this fashion enables a reduction in the amount of weight borne by the patient. There are also safety advantages (e.g. the patient cannot fall down while being held up by the harness). In an embodiment where the harness bears the entire weight of the patient, the exercise apparatus can provide resistance to facilitate training. Optionally, the apparatus provides resistance in the absence of the harness or if the weight is only partially borne by the harness. Resistance can also be added to the exercise routine by affixing weights to the patient. The third optional mode is a combination of the two, whereby the patient is supplying motive force while being assisted by the rehabilitation apparatus. In the third optional mode, the rehabilitation apparatus optionally supplies additional force to a patient's actions on various apparatus components, such as a foot pedal. Optionally, the apparatus nudges the patient, as in the case of the support chair 702 when assisting the patient with standing up.

Optionally, the patient may be supported or partially supported while in any of the three modes. Also, it should be noted that these three modes of operation can be applied to any of the actions 202-212 of the rehabilitative process and while they are characterized as likely at the beginning and likely towards the end of rehabilitation, the modes can be used at anytime as is desired and/or necessary for rehabilitating the patient.

It should be noted that different modes may be applied to different movements in a same exercise. For example, translation movement of the foot pedal may be restrained or free, while angular motion is constrained (or resisted) according to what a correct (or exercise-correct) rotation of the pedal would be during such a translation. Similarly, translation motion in one or two axes may be forced to match the effect of rotational motion and/or of applied force of the patient's foot.

In an exemplary embodiment of the invention, hip and torso movement relative to leg motion is measured in order to gauge the patient's needs for rehabilitation using them in combination, to rehabilitate the patient's use of all three together and in order to ascertain the patient's progress in using them in concert.

At action 206, hip motion exercises and analysis are included in gait rehabilitation in an exemplary embodiment of the invention. As a patient progresses from sitting to standing to walking, proper hip movement becomes important. One way to rehabilitate hip movement is to use sensors to monitor the hips as the patient performs rehabilitation exercises. Optionally, the sensors are attached to a rehabilitation apparatus like a harness in which the patient is strapped. As the patient proceeds to take steps the harness sensors detect swing motion of the patient where the motion of the patient may be unbalanced or insufficiently supported by the patient's body parts. Analysis of the swing data can provide the patient with instructive information on improving hip angle and positioning. In some exemplary embodiments, a specially adapted chair is used to support and measure hip motion during rehabilitation. Optionally, exercises are provided in which the patient moves the hip in order to assist the passive motion of a paretic leg. In an exemplary embodiment of the invention, a belt is used with a plurality of recoiling wires wherein each wire length is measured (e.g. by encoder or potentiometer) and thus accurate location of the hip is provided to the system. Optionally, the wires support and/or manipulate the hip to provide hip guidance.

Shoulder motion is rehabilitated and optionally analyzed at action 208. An optical sensing device, such as a camera, and/or sensors can be used to detect and record shoulder movement of the patient in order to provide a baseline of performance and to monitor the progress of the rehabilitation of this element. As with the hip embodiment, wires can be used to measure shoulder position and location and can also optionally be used to provide support and/or manipulation of the shoulder. In an exemplary embodiment of the invention, position sensors are attached to the patient's body which signal movement of the patient to a controller. The sensors are optionally wireless. In some exemplary embodiments of the invention, the cameras are used to image detect the limbs of the patient and/or patches affixed to the patient which move when the patient is in motion. Recorded shoulder movement can be compared to a goal movement profile or previous recordings of the patient's movement for analysis. Optionally, this record and playback or comparison technique can be used for any step of rehabilitation. Optionally, the patient imitates a previously recorded movement profile which is presented to the patient during rehabilitation and which functions as the goal movement profile. The previously recorded movement profile can be from the patient's movement or that of another. Optionally, the movement profile is generated by the controller.

The shoulders play an important role in a patient's gait, for example with regards to arm movement. In an exemplary embodiment of the invention, articulated robotic arms are affixed to the patient which assist the movement of the arms and shoulders in combination. Optionally, the patient is attached to the robotic arms through the use of restraints. The patient can be attached to the robotic assistance at any part of the body that will provide suitable rehabilitation exercise to the patient. In some exemplary embodiments of the invention, the patient is not affixed to the robotic assistance, but rather, holds on to the robotic apparatuses for movement guidance. The movement trains the arms and shoulders to move under various conditions like walking, stair climbing, etc. Optionally, the exercises provided to the patient are varied depending on the patient's need for rehabilitation. An example of an exercise for rehabilitating shoulders is moving the patient's arms and shoulders in a skiing motion. Robotic assistance can be optionally provided on either or both sides of the patient, above and/or below the patient or in front of and/or behind the patient. Optionally, robotic assistance is provided utilizing a combination of these locations. For example, a robotic arm is located on each side of the patient and is either affixed to or is grasped by the exercising patient. As the patient exercises, the robotic arms can guide the patient in moving his/her arms appropriately (e.g. while walking).

Arm movement is rehabilitated at action 210 in an exemplary embodiment of the invention. As in the previous rehabilitation steps, cameras, sensors, or even a robotic arm, can detect and/or record arm motion. In the passive mode, the arm(s) needing rehabilitation are moved by the rehabilitation apparatus along a recommended path of motion. In assisted mode, the patient supplies some modicum of arm movement with input from the rehabilitation apparatus as needed.

In an exemplary embodiment of the invention, action 212 reinforces individual gait element improvement within the context of some or all of the elements cooperating with each other. For example, it is desirable to train coordinated leg and arm movement in some embodiments of the invention (i.e. left leg forward means right arm forward). As described above, coordinated movements such as walking and simulated skiing, for example, can be exercised by the patient in order to rehabilitate combination movements of the various body elements. Another combination movement that is exercised in an exemplary embodiment of the invention is turning. Optionally, coordinated movements and/or gait can be assisted by playing rhythmic music to the patient during exercise.

In an exemplary embodiment of the invention, the patient moves a healthy body part on one side, which is recorded (and possibly filtered and/or modified depending on the rehabilitation needs of the patient) and then the healthy movement is "played" to the paretic side by the rehabilitation apparatus, thereby imparting the patient's natural gait to the body part being rehabilitated through kinesthetic feedback. Optionally, the apparatus "plays" the nominal gait to the paretic body part, so the patient gets the feel of the nominal movement, then the patient repeats the movement using the paretic body part, either with assistance or without assistance from the apparatus.

In exemplary embodiments of the invention, these exercises can be performed either sitting or standing, or while suspended from a weight relieving apparatus such as a harness. It should also be noted that patients will present themselves requiring varied degrees of gait rehabilitation and therefore some exercises are not required or desirable. For example, some patients will present themselves not being confined to a wheelchair or a sitting position, or need only rehabilitation on one side. Optionally, a patient who is missing at least one limb has their gait rehabilitated utilizing at least one prosthetic limb.

Figure 7:
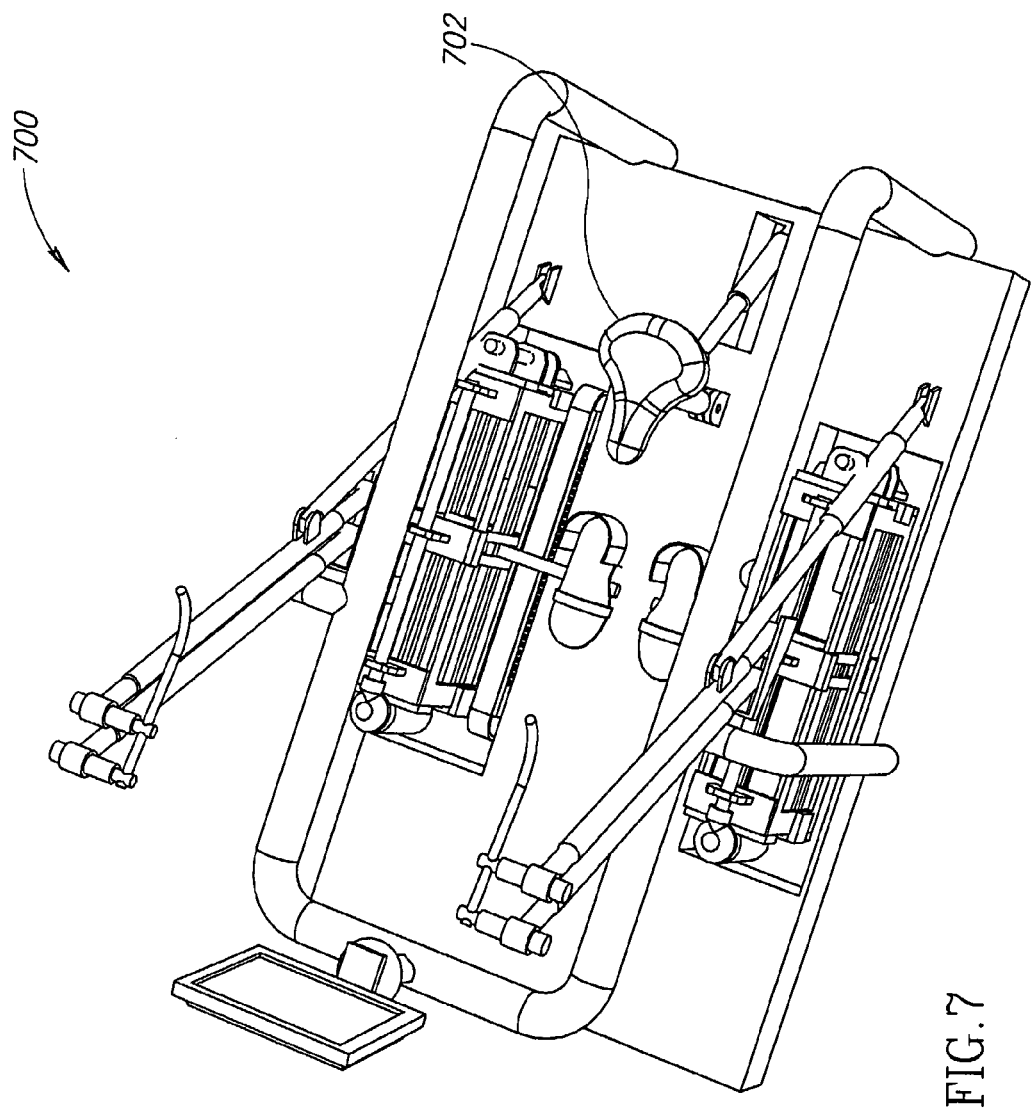
FIG. 7 is a view of a rehabilitation apparatus being used in conjunction with a support chair in an exemplary embodiment of the invention.

Optionally, a patient can perform these exercises with an object designed to assist with movement (e.g. a wheelchair, a walker, crutches, ski poles, walking stick or a cane). In an exemplary embodiment of the invention, when a patient is using wheelchair, a support chair, such as the type depicted in FIGS. 7 and 8, is not required. The wheelchair is moved into position on an apparatus and exercise can be performed from the seated position in the wheelchair, or the patient can be assisted to a non-seated exercise position as described herein. In some exemplary embodiments, the frame of an apparatus swings open to allow entry of a wheelchair or walker. Patients requiring the assistance of crutches or a cane can exercise in an apparatus which is adapted to be wide enough to provide side room for the walking appliances. It should be noted that in some exemplary embodiments of the invention, walking appliances used in conjunction with the apparatus may be slightly longer than would normally be used to account for the foot pedals being slightly off the floor.

In an exemplary embodiment of the invention, exercise from the standing position is provided. As described herein, measurements can be made of a variety of patient parameters, including position of and amount of force being exerted on each body part. In a standing position, it can be measured how much relative weight is being supported by each leg. Additionally or alternatively, if the patient is not capable of standing without support, weight borne by other body parts is also measured. In an exemplary standing exercise, the patient is nudged from a stable standing position into an unstable on (i.e. out of balance). The patient then exercises by restoring his or her balanced standing position. Optionally, at least a portion of the patient's weight is supported by a rehabilitation apparatus. In an exemplary embodiment of the invention, patient movement and exerted force is measured in order to calculate any deficiencies in the patient's stance. Optionally, feedback is provided to the patient during exercise in order to facilitate rehabilitation. For example, if too much weight is being placed on a leg during an exercise, the rehabilitation apparatus signals to the patient to take some weight off of the leg and therefore add more weight to the other leg. In an exemplary embodiment of the invention, feedback is based on the measurements of the patient's positioning and force exerted, as described herein.

In an exemplary embodiment of the invention, a rehabilitation apparatus, such as those described herein, is moved by the patient in order to measure the patient's gait while performing various activities (e.g. walking or running). The patient is first placed into an exercise position in a rehabilitation apparatus and then is instructed to commence a particular motion, such as walking. As the patient moves, the apparatus optionally records the movement. The recorded movement is optionally analyzed to identify deficiencies in the patient's gait, and therefore assists with preparing a rehabilitation program. Additionally or alternatively, the movement record can be used as a benchmark of the patient's performance, for the purposes of tracking the patient's improvement for example. In an exemplary embodiment of the invention, the apparatus used to measure the patient's movement is the same apparatus used to provide exercise. Optionally, a separate machine is used to measure the patient's movement.

Figure 3:
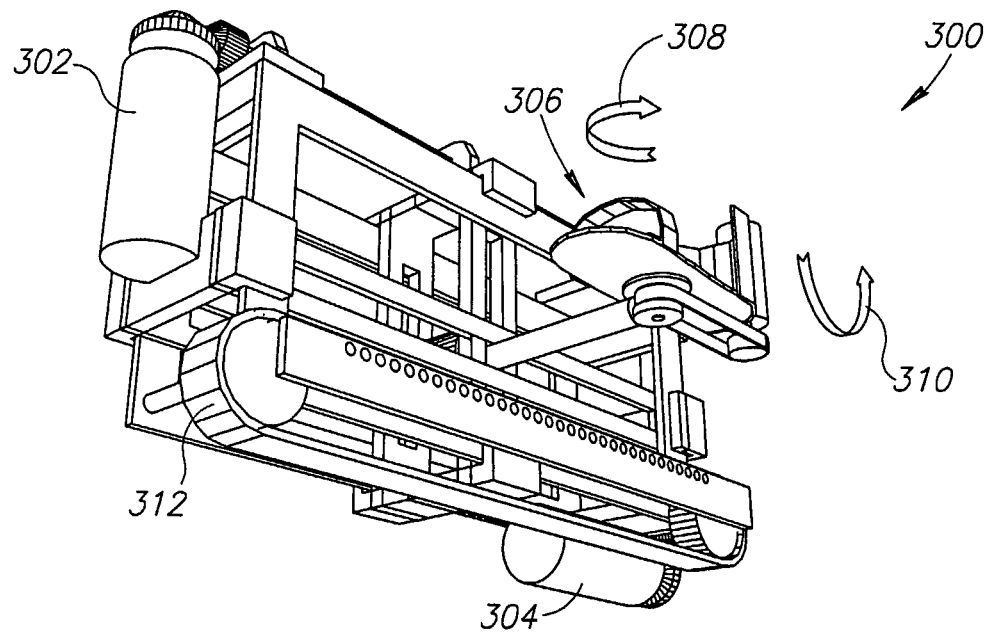
FIG. 3 is an illustration of a portable side rehabilitation apparatus in accordance with an exemplary embodiment of the invention.

Referring now to FIG. 3, an illustration of a portable side rehabilitation apparatus 300 in accordance with an exemplary embodiment of the invention is provided. The apparatus 300 is optionally utilized to rehabilitate the gait of a patient in conjunction with the methods described in FIGS. 1 and 2. In an exemplary embodiment of the invention, the portable side rehabilitation apparatus 300 operates in the x and z axes. In this embodiment, x-axis means that from the patient's point of view, the positive x-axis extends in a straight forward direction of travel for the patient. The z-axis in this embodiment means that from the patient's point of view, movement is up is in the positive z-axis and down is in the negative z-axis. Located on the apparatus 300 are motors 302 and 304 for providing movement to components of the apparatus 300 along these axes. A patient being rehabilitated straps a foot into a foot pedal 306 which is provided to move in both the x and z axes. In addition to x and z axial movement, in an exemplary embodiment of the invention, the foot pedal 306 rotates in multiple directions as depicted by arrows 308 and 310 in FIG. 3. Optionally, the foot pedal 306 can be equipped with pressure sensors in order to gauge and analyze the patient's force applied on at least one location by and/or on the foot.

In an exemplary embodiment of the invention, the foot pedal 306 has the capability to extend and retract along the y-axis of FIG. 3. Patient turning can be exercised by utilizing at least the rotational and extension capabilities of the foot pedal 306 while the patient follows a hypothetical curved path. Optionally, turning is exercised by widening the stance of the patient during exercise.

While one of the patient's feet is strapped into the foot pedal 306, the other foot can be at rest, on a treadmill-like track 312 or even on a second foot pedal, similar to foot pedal 306. When a person commences movement the foot is either in the air moving forwards or is supporting the patient weight. In an exemplary embodiment, the implementation of the track 312 allows the use of the motor only for the first segment (moving forward). This method of rehabilitation optionally enables the use of a smaller motor because the whole body weight is not supported by the foot being moved, rather it is borne on the foot on the treadmill. The resultant effect of this condition is that the motor only has to move the weight of the foot that is moving forward and not the whole body weight, allowing for less power to be used. In some exemplary embodiments, the track 312 can be wider to accommodate the foot not being exercised. In such an embodiment, the x-z mechanism moves the paretic foot while the track 312 provides a treadmill like activity for the other foot. Therefore, in some exemplary embodiments of the invention, only one side of the patient is exercised.

In an exemplary embodiment of the invention, track 312 is used to move the pedal, rather than the other foot as just described (however, two treadmills may be provided). In this embodiment, when the pedal is at its lowest Z position, the patient is expected to lay full weight on the pedal. Alternatively or additionally to providing a strong Z-axis motor, track 312 is used to support the weight of the pedal. Optionally, the track is motorized and moves the pedal. A smooth rail maybe used instead of the belt track shown. Optionally, the rail is replaceable with rails of other shapes, for example, slightly curved. Optionally, a slotted plate is provided with the pedal being constrained to travel within the slot. Optionally, the slot defines a closed loop. Optionally, the plate is replaceable. Optionally, if a narrow slot is used, a single motor may suffice to move the pedal.

Optionally, if the patient lays his weight on the pedal while it is being lifted, the patient is signaled that he is not walking correctly and the motor stops and does not need to support the weight of the patient. Alternatively or additionally, power is traded for accuracy (e.g., using a gear) as such patients may not have a need for accurate movement.

The patient may be optionally standing or sitting while using the apparatus 300. For example, a patient sitting down can use the rotational ability of the foot pedal 306 to build strength and control in the foot and lower leg. In some exemplary embodiments of the invention, the apparatus 300 is provided with anti-tip extending legs, which provide stability to the patient strapped into the apparatus as well as the apparatus. Optionally, the foot pedal 306 can be inserted from either side of the apparatus 300. In an exemplary embodiment of the invention, switching the side from which the foot pedal is inserted can provide exercise movement for both sides of the patient without having to substantially move the apparatus. In some exemplary embodiments, the apparatus 300 is adapted to be used in the water. Use in the water is accomplished by waterproofing components of the apparatus which are sensitive to water. This may include encapsulating any sensors being used and/or using waterproof sensors. Optionally, the apparatus can be hydraulically operated to take advantage of the ample water supply. In exemplary embodiments of the invention, the travel in the z axis is only a few centimeters and the travel (i.e. step) in the x-axis is only approximately 20-50 centimeters, therefore the apparatus can be low to the ground and relatively short in length. In an exemplary embodiment of the invention, the low profile of the apparatus allows it to be used with a chair. As a result, an additional optional feature of the apparatus 300 is that it is portable. Optionally, the foot pedal 306 is provided with quick release bindings, like ski bindings, to avoid unwanted motion being imparted to the patient. Thus, in some embodiments of the invention a lower power motor is used for moving the patient's leg that is being rehabilitated, since the patient's body weight is not being supported on it. Use of a lower powered motor, and hence smaller/lighter motor, also enhances the portability of the apparatus 300. Various power sources can be used including, but not limited to, battery and/or AC or DC current.

In an exemplary embodiment of the invention, the foot pedal 306 is attached to the apparatus 300 not from the side, as depicted in FIG. 3, but from the bottom of the foot pedal, maintaining the previous functionality of the apparatus 300.

Optionally, the apparatus 300 is used in concert with prosthetic limbs, for example a prosthetic foot or leg. The prosthetic devices are either secured to the apparatus before the patient mounts the apparatus 300 or, in the alternative, the devices are attached to the patient before the patient gets on the apparatus. Optionally, rehabilitation exercises are modified to account for the use of prosthetics. In an exemplary embodiment of the invention, the patient exercises both the natural leg and the prosthetic leg together. In an exemplary embodiment of the invention, the patient exercises a prosthetic limb in coordination with other body parts. In an exemplary embodiment of the invention, exercise is performed with the assistance of a walking aid such as a cane, crutches or a walker.

Figure 4:
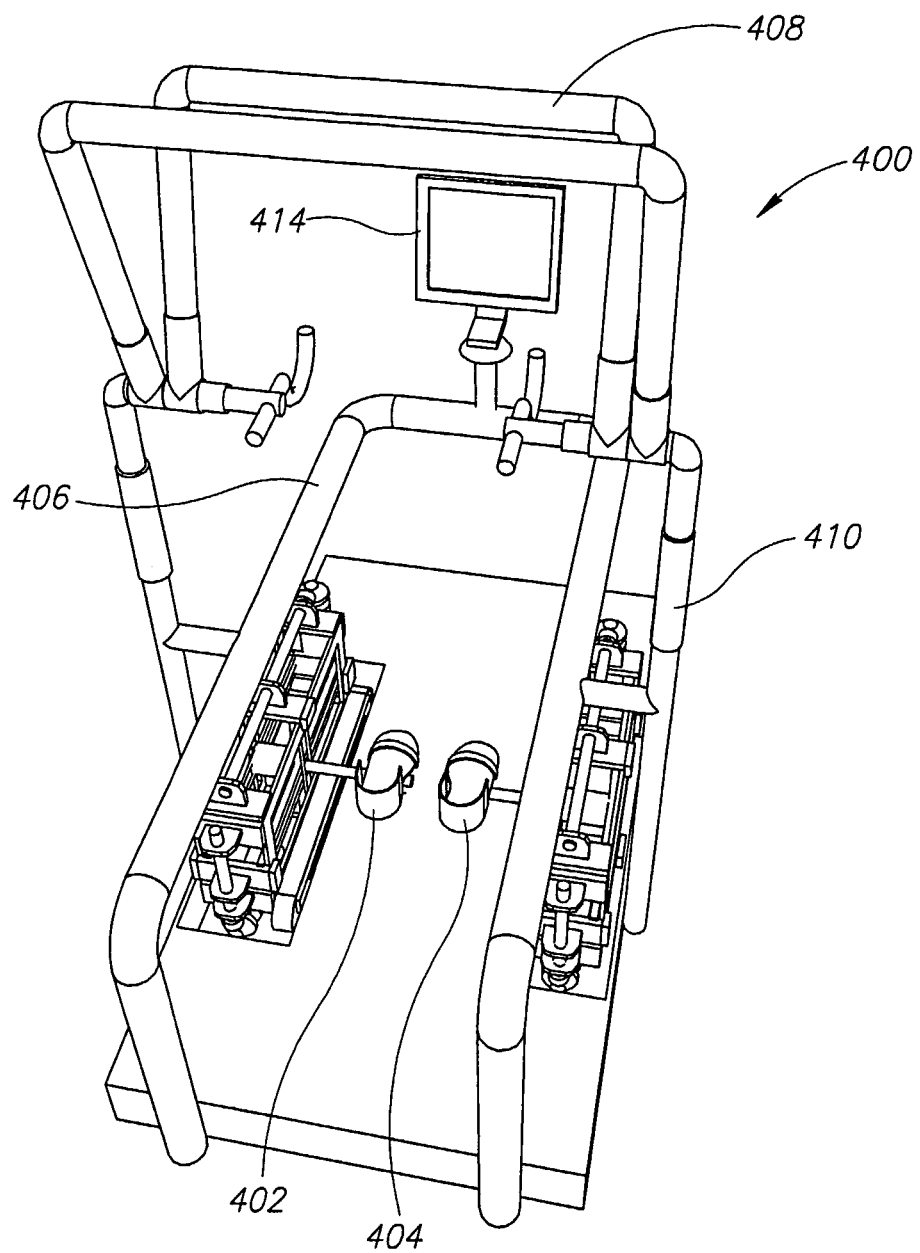
FIG. 4 is an illustration of a two-sided rehabilitation apparatus in accordance with an exemplary embodiment of the invention.

An illustration of a two-sided rehabilitation apparatus in accordance with an exemplary embodiment of the invention is depicted in FIG. 4. The apparatus 400 can be used with the methods for gait rehabilitation described in FIGS. 1 and 2. In this embodiment, an apparatus 400 is provided with a left foot pedal 402 and a right foot pedal 404. Optionally, this apparatus 400 allows movement of the foot pedals 402 and 404 in the x and z axes. The apparatus 400 also includes a frame 406 in some exemplary embodiments. Sensors are optionally attached to the frame 406 in order to measure the motion of legs, hips, shoulders, and/or arms relative to walking points. These sensors are optionally operatively connected to a data processing device for analysis of the motion recorded and for planning rehabilitation. In certain exemplary embodiments, a camera is used to track the patient's movement.

Figure 5:
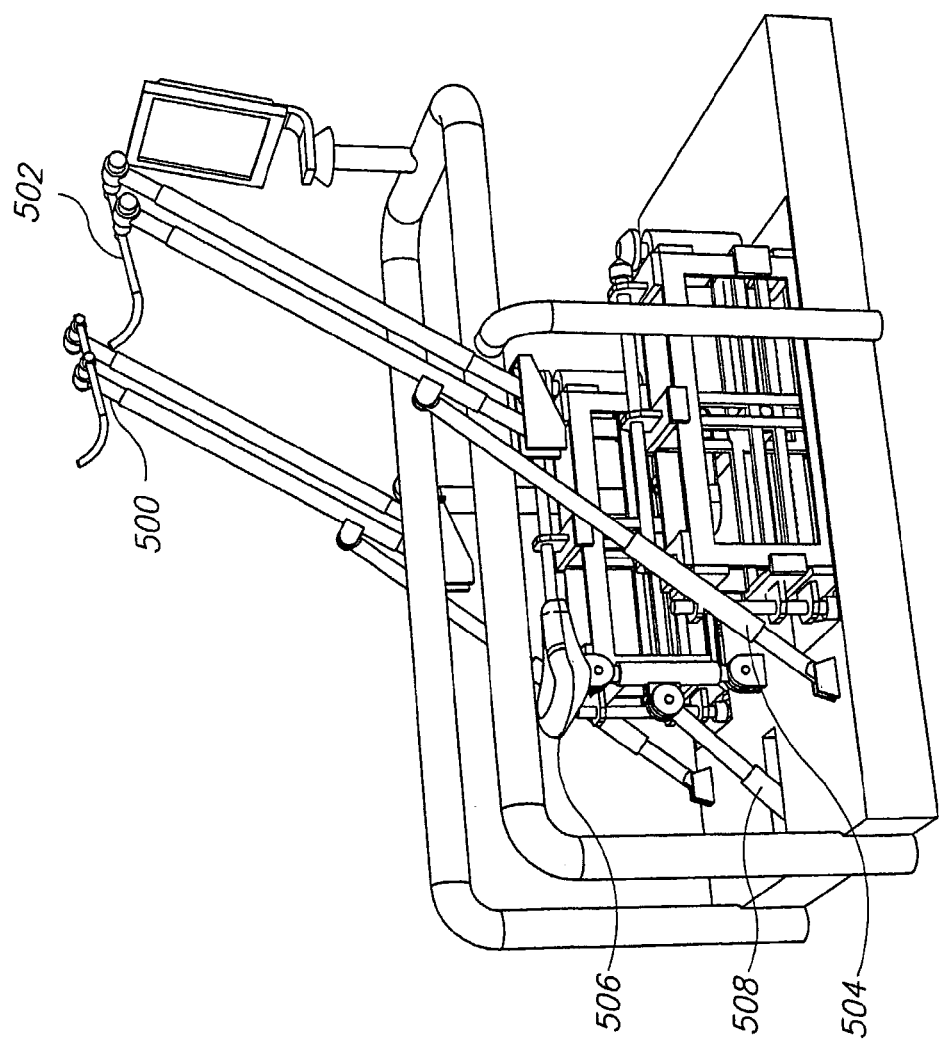
FIG. 5 is an illustration of a two-sided rehabilitation apparatus using adjustable handling bars in accordance with an exemplary embodiment of the invention.

The frame 406 is modified in some embodiments to include an upper structure 408 which can include a vertical adjustment system 410, for taller or shorter than average patients (e.g. children), or body weight support apparatuses such as a harness 602 (depicted in FIG. 6), hangers, or bars 500 (depicted in FIG. 5). In some embodiments of the invention, the vertical adjustment system 410 is adjustable to provide varying levels of supporting force to the patient. In some exemplary embodiments, the frame 406 is also provided with a display unit 414. The display unit 414 can function as a television, or it can contribute to the rehabilitation of the patient by incorporating games which stimulate particular exercises, display exercise related data, provide virtual reality experiences (e.g. kicking a ball, climbing steps, avoiding obstacles) or even just projecting scenery (e.g. walking in the park) into the routine. Optionally, the apparatus 400 provides a support chair 702 (depicted in FIGS. 7 and 8). In some exemplary embodiments, the apparatus 400 can be used in water. Optionally, real objects are used in conjunction with the rehabilitation of the patient (e.g. a real ball is kicked by the patient, a step is placed on the apparatus which the patient must overcome).

In an exemplary embodiment of the invention, patients' rehabilitation is assisted by feedback based on a target movement profile in view of their current movements. Feedback can be in the form of beeps and/or visual cues and other similar video and audio prompts. This is particularly useful for patients with Parkinson's who have a gait problem because they cannot properly gauge step size. Through feedback, the proper step size can be relearned. Feedback is optionally implemented with any of the methods and/or apparatuses described herein. For example, in an exercise where the patient imitates a movement seen on the display, or imitates a previously recorded movement profile, the patient can be guided through exercise via kinesthetic feedback as the controller senses patient movement, calculates deviation from the goal movement profile, and prompts the patient to move according to the goal profile. Optionally prompting is achieved through vibration. Optionally, prompting is performed by the apparatus actually moving or nudging the patient in the appropriate direction. Optionally, varying levels of feedback and exercise instruction are provided to the patient based on the patient's cognitive state. For example, for patients with low cognitive abilities, more simple instructions and/or more forceful feedback is optionally provided.

In order to accommodate patients who would have trouble mounting a rehabilitation apparatus 400, the apparatus 400 optionally incorporates features to make entry and exit more feasible, and reduce need for human help. In some embodiments of the invention, the two sides of the frame 406 can swing open in order to allow entry and exit of a patient (particularly in the case where a patient is wheelchair bound). Optionally, the sides of the frame 406 swing open during exercise to allow the patient to "bail out" of the apparatus. Optionally, a belt can be used to pull the patient into an exercise position in the apparatus 400. FIG. 5 depicts how a patient can be raised into exercise position by using bars 500 with armpit supports 502 and at least one piston (or linear actuator) 504 to raise and lower the bars 500. Initially, a patient is seated on chair 506. While the patient is seated, the patient's arms are placed over the armpit supports 502. The patient is then lifted from a seated position by using at least one piston 504 to raise up the bars 500. The patient hanging from the armpit supports 502, is thusly lifted from the seated position. In some exemplary embodiments, the invention utilizes a chair 506 which tips and/or raises the patient into exercise position. Optionally, piston 508 is used to raise and lower the chair. Optionally, the chair's rear moves up in relation to the chair's front, thereby "tipping" the patient into exercise position. Optionally, no chair is used in the rehabilitation of the patient. Additionally or alternatively, a chair is used in the rehabilitation of the patient which is not part of the rehabilitation apparatus.

Figure 6:
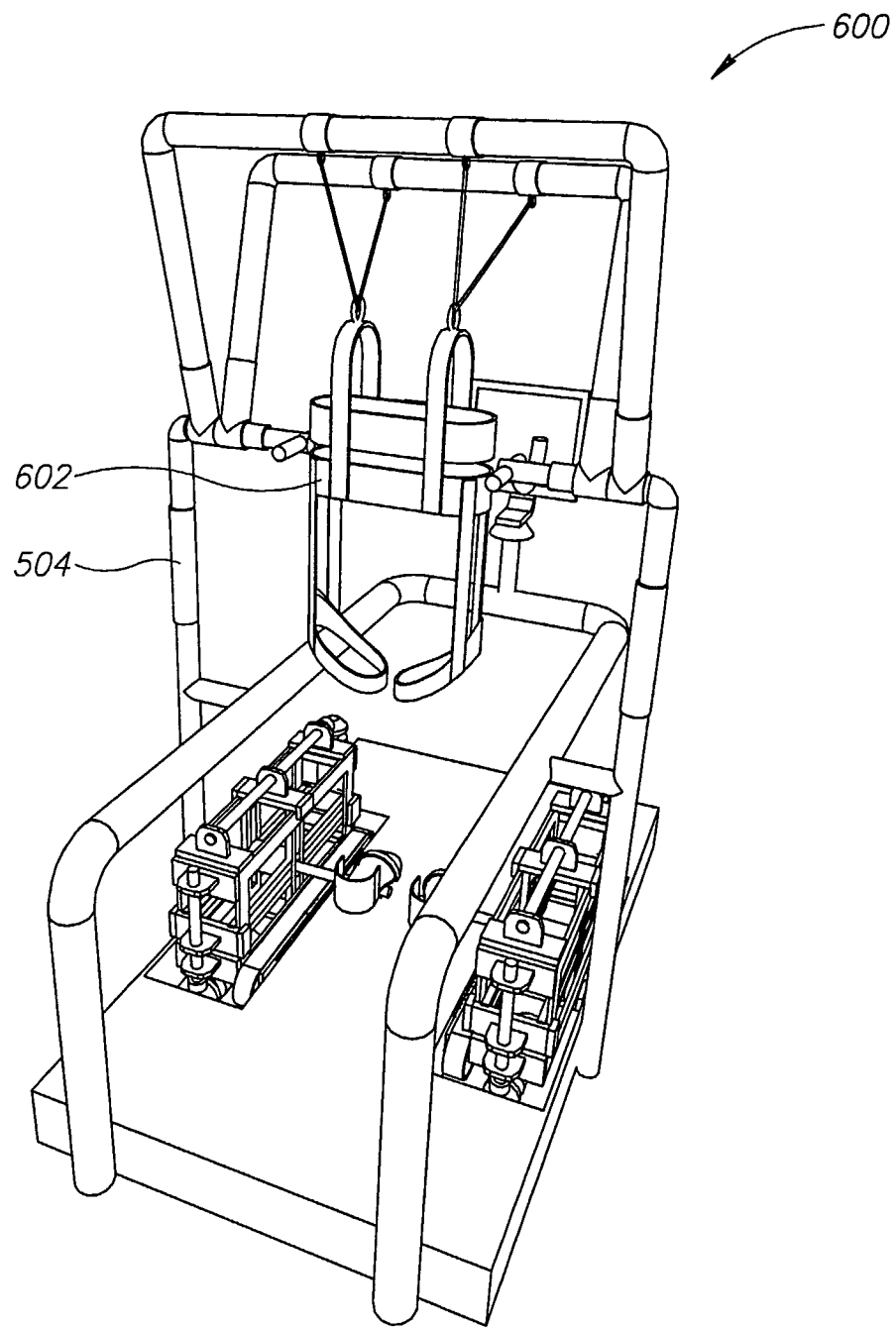
FIG. 6 is a view of a rehabilitation apparatus being used in conjunction with a support harness in an exemplary embodiment of the invention.

FIG. 6 depicts a rehabilitation apparatus 600 which can be used in the methods described in FIGS. 1 and 2 in order to rehabilitate the gait of a patient. In some exemplary embodiments of the invention, the apparatus 600 is provided with a harness 602 which supports some or all of the weight of the patient being rehabilitated. One use of the harness 602 is to measure and analyze a patient's gait while the patient is attached to the harness. In an exemplary embodiment of the invention, a patient is partially suspended from the harness 602 and commences forward walking motion. Partial suspension is achieved by first identifying a target weight at which the patient is to exercise. Second, a pressure sensor measuring the patient's exerted pressure on the apparatus and/or a weight sensor on the harness is indexed while the harness with the patient inside is moved away from the apparatus until the goal weight is achieved. In an exemplary embodiment of the invention, movement of the harness away from the apparatus is conducted slowly and with a delayed response to prevent unwanted patient movement during exercise. While the patient is moving, the harness 602, which is operationally connected to sensors, monitors the patient's gait. The sensors may optionally monitor the patient's position, acceleration, force, and/or velocity. The data output by the sensors is analyzed and thus, anomalies in the gait are detected, either by the controller or by a healthcare professional. From this data analysis of the gait, it can be determined where improvements need to be made. Optionally, the controller gives advisory instructions on how to improve the patient's gait. Optionally, the patient's gait is played back in slow motion for detailed review. Optionally, gait analysis includes comparison of movement to measurements conducted by a neural network. In some exemplary embodiments, a patient strapped into a harness 602 is lifted into exercise position by using at least one piston 504. Optionally, the piston 504 measures and/or adjusts the amount of support delivered to the patient during exercise. Another use of the harness 602, optionally in combination with piston 504, is to allow the patient to exercise without bearing the patient's full weight on the rehabilitating limbs. As strength and control return to the patient, weight can be gradually added until the patient is bearing full weight. In an exemplary embodiment of the invention, weights are added to the exercise routine to increase resistance to movement.

Turning now to FIG. 7, a rehabilitation apparatus 700 can be seen being used in conjunction with a support chair 702. In alternate embodiments of the invention, the chair 702 is provided with the ability to move up and down, rotate in various directions and is provided with a separate back support. In exemplary embodiments of the invention, altering the chair position allows for the exercise of different components of the patient without having to fundamentally change the configuration of the apparatus. As mentioned previously, the chair 702 may optionally also tip forward, assisting a patient into and out of an exercise position. Optionally, the chair allows free leg movement.

Figure 8A:
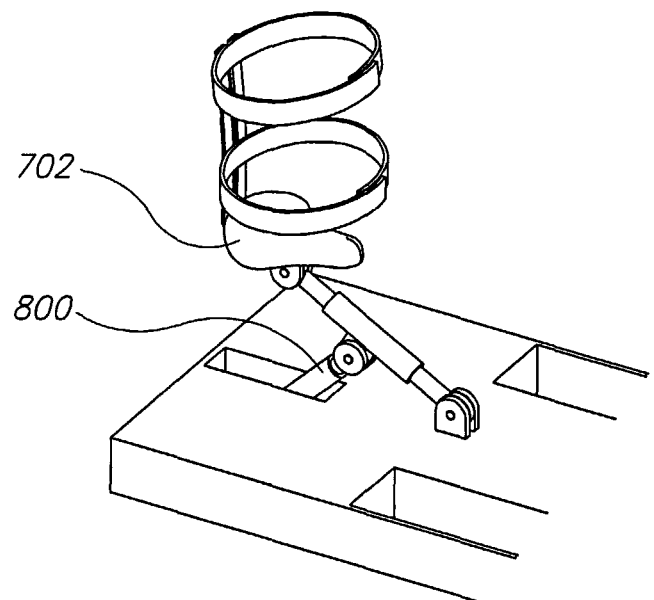
FIGS. 8A-C are views of various modes of operation of a support chair in an exemplary embodiment of the invention.
Figure 8B:
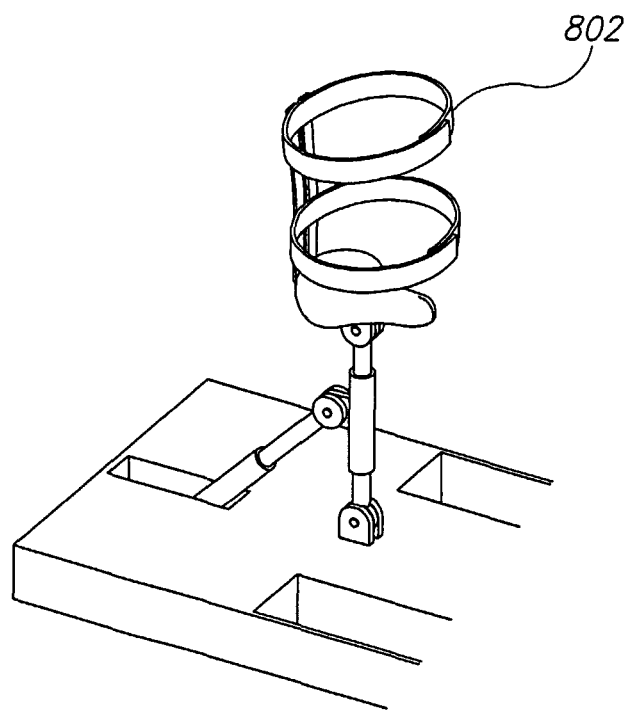
Figure 8C:
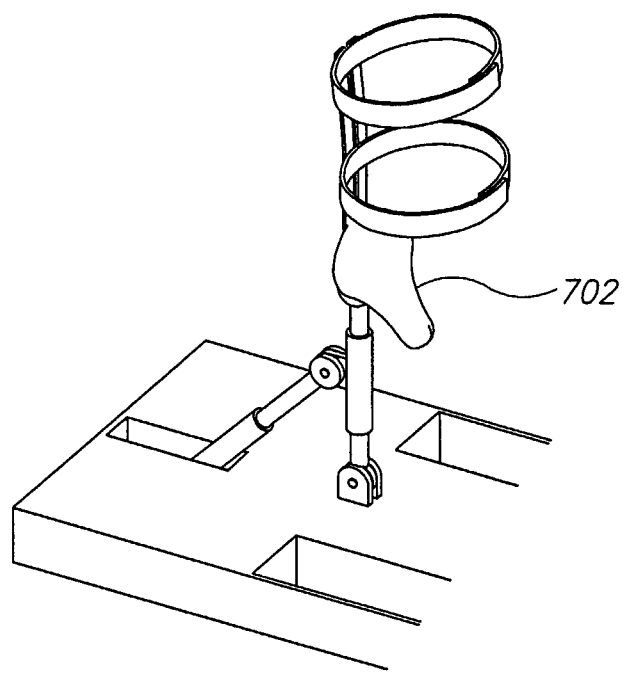

FIGS. 8A-8C depict a support chair 702 in further additional embodiments of the invention. FIG. 8A shows a chair which can be lowered by a piston 800. Lowering of the chair can assist the patient into a rehabilitation apparatus or can be incorporated into a particular exercise for rehabilitating gait. FIG. 8B shows the chair 702 in a higher position than in FIG. 8A. In exemplary embodiments of the invention, the chair 702 moves up and down depending on the individual needs of the patient. It can also be seen that a torso support 802 can be optionally included with the support chair 702. In an exemplary embodiment of the invention, the torso supports open to allow the entry of a patient into the chair. FIG. 8C depicts the support chair 702 in a fully "tipped" condition whereby in some exemplary embodiments of the invention a patient is assisted into exercise (standing) position by a tipping support chair. In an exemplary embodiment of the invention, the chair 702, and optionally other rehabilitation apparatuses, is used to evaluate and teach a patient how to rise from a sitting position to a standing position. During this exercise the patient is optionally supported, partially supported or not supported depending on the needs of the patient. Optionally, the chair 702 is used by the patient to rest before, during or after exercise. Optionally, the chair 702 can be supported on a gimbal.

As described above, various sensors can be affixed to the patient and/or the various rehabilitation apparatus components in order to accurately gauge the progress of the patient's rehabilitation in exemplary embodiments of the invention. A wide variety of sensors can be used either alone, or in combination, for this purpose. The sensors can be loosely divided into two types: the first are sensors pertaining to the patient (e.g. body part location, physiological responses), while other sensors are used to gauge the disposition of the chair (e.g. position/orientation of chair components).

In order to gather information on the patient during rehabilitation, sensors are optionally attached to the patient's body. For example, positional sensors are optionally attached to body parts such as the arms, chest, head, feet, hands, and/or legs. These positional sensors are used to determine the location of the various body parts while exercising. Analysis of these location measurements assists with recognizing overall patient movement, including overcompensation for weak body parts by stronger body parts and the like.

Another type of sensor that is optionally used during a patient's rehabilitation is a pressure sensitive sensor. Through the measurement of a patient's exerted pressure in a particular location (e.g. foot pedal 306 and/or multiple sensors on patient), it can be determined how dependent the patient is on that body part for stability and/or body control. Pressure sensors are optionally used with the hands, legs, feet, arms, rear end, head, and torso. In an exemplary embodiment of the invention, analysis of the collected pressure data illustrates if the patient's gait is balanced, and if not, where the deficiencies in the gait are situated. An inordinate amount of pressure on one leg for example would tend to indicate that the patient can't adequately use the other leg. The patient's rehabilitation program could then be tailored to work on balance the use of both legs to overcome the deficiency. Force can optionally be measured using pressure sensors. A patient who extends towards a target can activate a pressure sensor which detects how much pressure (i.e. force) the patient could exert on the target. In an exemplary embodiment of the invention, pressure sensors are used for measuring both strength and balance in combination.

In an exemplary embodiment of the invention, other sensors, such as muscle tension and electromyography ("EMG") sensors are used to monitor a patient's physiological responses to rehabilitation. Analysis of measurements taken from these sensors help identify which parts of the patient require further rehabilitation and allow planning of future rehabilitation strategy. Optionally, pulse measurement or breathing rate sensors are used.

In addition to or alternatively to sensors for monitoring the patient, sensors are optionally provided for monitoring the operation of a rehabilitation apparatus in an exemplary embodiment of the invention. Sensors are optionally affixed to any component of the rehabilitation apparatus for tracking the position of those components. One type of sensor of this purpose is a magnetic-based position tracking sensor. Ultrasonic, motor encoders, potentiometers and optical position sensors are known as well. Of particular use is comparing sensor readings from the apparatus with sensor readings from the patient. Comparative analysis of this data indicates patient response to specific movements from the apparatus. Deficiencies in the patient in response to these apparatus movements point to areas needing further rehabilitation.

Optionally, all of the methods and apparatuses described herein can be used with children, teenagers, adults, young and old alike. Optionally, all of the methods and apparatuses described herein are altered depending on the patient's physiological profile, including factoring in amputations, if any. Optionally, all of the methods and apparatuses described herein are adapted for use by patients who require electrical control of at least one body part (e.g. patients with spinal cord injury).

Training of gait is not limited by the particular examples shown above. In particular, gait rehabilitation can be used, for example for supplementing the fine motor control rehabilitation methods described in U.S. Provisional Patent Application No. 60/566,079, the disclosure of which is incorporated herein by reference. For fine motor control, a particular gait should be maintained by the patient while applying fine motor control. Fine motor control tasks can be carried out while sitting down.

Gait rehabilitation can also be combined with neural rehabilitation. For example, U.S. Provisional Patent Application No. 60/604,615, the disclosure of which is incorporated herein by reference uses neuronal sensing to determine when an action should be triggered. EEG signals can be used as feedback for gait-related activities.

Gait training can be used with EMG. For example, U.S. Provisional Patent Application No. 60/566,078, the disclosure of which is incorporated herein by reference, gait sensing can be used in addition to EMG or to determine when EMG should be delivered.

Gait training can be used with balance training, for example such as described in U.S. Provisional Patent Application No. 60/633,442, the disclosure of which is incorporated herein by reference. In one example, sitting balance training is used prior to or as an adjunct to gait training.

Music can be used for balance training, for example such as described in U.S. Provisional Patent Application No. 60/633, 429, the disclosure of which is incorporated herein by reference. In one example, music is used to indicate balance between body sides. A channel which is too loud may be used to indicate a body portion applying too much force. Silence may be used to indicate balance, while a wobble will generate a cyclical tube and as balance is lost and alarm may increase in amplitude.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. When used in the following claims, the terms "comprises", "includes", "have" and their conjugates mean "including but not limited to". It should also be noted that the device is suitable for both males and female, with male pronouns being used for convenience. The scope of the invention is limited only by the following claims.

The invention claimed is:

1. A method for gait rehabilitation, comprising:
identifying at least one deficient gait element;
attaching a pedal rotatable, independent from rotational motion applied to it by at least one motor of a rehabilitation apparatus, in a plurality of axes to a foot of a patient;
exercising said deficient gait element individually using the rehabilitation apparatus to automatically control the rotating of said pedal using motorized rotation in combination with independent pedal rotation while rehabilitating said patient; and,
exercising said deficient gait element through the pedal in concert with at least one other gait element in more than one plane on the same side of the body, using said rehabilitation apparatus,
wherein the rehabilitation apparatus provides exercising in at least one of three modes, the first where motive force is solely derived from the patient, the second where motive force is solely derived from the rehabilitation apparatus and the third where motive force is derived as a combination from the patient and the rehabilitation apparatus.

2. A method of claim 1, wherein gait elements are chosen from a group consisting of feet, legs, hips, torso, shoulders, head, hands and arms.

3. A method of claim 1, further comprising exercising a complex gait.

4. A method of claim 3, wherein a complex gait is chosen from the group consisting of balance, overcoming obstacles, moving backwards, movement on steps, turning, movement on slopes and varying speed.

5. A method of claim 1, wherein said gait rehabilitation is performed sitting down.

6. A method of claim 5, wherein said gait rehabilitation is performed in a wheelchair.

7. A method of claim 1, wherein said gait rehabilitation is performed utilizing an object designed to assist with movement.

8. A method of claim 7, wherein said object is selected from a group consisting of a walker, crutches, ski poles, a walking stick or a cane.

9. A method for gait rehabilitation according to claim 1, wherein the identifying at least one deficient gait element comprises:
detecting the positions of at least one gait element during movement;
recording the detected positions of the at least one gait element, wherein position recordings are made; and,
displaying said position recordings of the at least one gait element.

10. A method of claim 9, wherein at least one position sensor is used for said detecting.

11. A method of claim 9, wherein at least one optical sensing device is used for said detecting.

12. A method of claim 9, wherein at least one position sensor and at least one optical sensing device is used for said detecting.

13. A method of claim 9, wherein said position recordings are of movements performed by a person undergoing rehabilitation.

14. A method of claim 9, wherein said position recordings are of movements performed by a person not undergoing rehabilitation.

15. A method according to any of claims 9, 10-14, wherein said exercising is analyzed in comparison to said position recordings.

16. A method of claim 15, wherein additional exercise is performed based on said analysis.

17. A method according to claim 1, wherein said rotating is in at least two axes.

18. A method according to claim 1, comprising automatically controlling the translation said foot during said rotating.

19. A method according to claim 1, wherein controlling the rotating comprises restricting the rotation range.

20. A method according to claim 1, wherein controlling the rotating comprises restricting the rotation angle.

21. A method according to claim 1, wherein controlling the rotating comprises applying a resistive force to rotation.

22. A method according to claim 1, wherein controlling the rotating comprises causing said rotation.

23. A method according to claim 1, wherein controlling the rotating comprises initiating said rotation and allowing the rotation to continue to completion of a desired amount.

24. A method according to claim 1, comprising rehabilitating two feet concurrently.

25. A method according to claim 1, wherein said pedal is movable in a plane perpendicular to a surface and wherein said automatically controlling the rotation is responsive to movement of said pedal in said plane.

26. A method according to claim 9, wherein exercising the at least one deficient gait element is based on said display of said recording.

27. A method according to claim 1, further comprising measuring rehabilitation progress.

28. A method according to claim 27, wherein measuring uses at least one EMG sensor.

29. A method according to claim 27, wherein measuring uses at least one optical sensing device.

30. A method according to claim 1, further comprising providing feedback during the exercising for enhancing gait rehabilitation performance.

31. A method according to claim 1, wherein identifying and exercising during gait rehabilitation are adapted for at least one of a child or an adult.

32. A method according to claim 1, further comprising transmitting exercise data to a remote location over a communications network.

33. A method according to claim 1, wherein exercising is performed with the apparatus set in at least one of a plurality of operational modes.

34. A method according to claim 33, wherein the at least one set mode is motive.

35. A method according to claim 33, wherein the at least one set mode is passive.

36. A method according to claim 33, wherein the at least one set mode is a combination of motive and passive.

37. A method according to claim 1, wherein the at least one deficient gait element is a complex gait element chosen from the group consisting of balance, overcoming obstacles, climbing steps, movement on slopes and varying speed.

38. A method according to claim 1, further comprising entertaining during exercising by incorporating at least one of: games which stimulate particular exercises; displaying exercise related data; providing virtual reality experiences; or, projecting scenery during the exercising.

* * * * *